United States Patent [19]
Reed et al.

[11] Patent Number: 5,659,024
[45] Date of Patent: Aug. 19, 1997

[54] PROMOTORS THAT REGULATE THE EXPRESSION OF GENES INVOLVED IN CELL DEATH

[75] Inventors: John C. Reed, Carlsbad; Toshiyuki Miyashita; Masayoshi Harigai, both of San Diego, all of Calif.; Motoi Hanada, Tsu, Japan

[73] Assignee: The Burnham Institute, La Jolla, Calif.

[21] Appl. No.: 330,535

[22] Filed: Oct. 27, 1994

Related U.S. Application Data

[63] Continuation-in-part of Ser. No. 182,619, Jan. 14, 1994, Pat. No. 5,484,710.
[51] Int. Cl.$^6$ .................................................. C07H 21/04
[52] U.S. Cl. ............................................. 536/24.1; 536/23.1
[58] Field of Search ................................. 536/23.1, 24.1

[56] References Cited

U.S. PATENT DOCUMENTS 5,362,623  11/1994  Vogelstein et al. ........................ 435/6

FOREIGN PATENT DOCUMENTS

WO92/13063  6/1992  WIPO .

OTHER PUBLICATIONS

Written Opinion, dated Nov. 14, 1995, in PCT Application PCT/US95/00710.
Funk, Walter D. et al., "A Transcriptionally Active DNA–Binding Site For Human p53 Protein Complexes." *Mole. Cell. Biol.* 12:2866–2871 (1992).
Ginsberg, Doron et al., "Wild–type p53 Can Down–Modulate the Activity of Various Promoters." *Proc. Natl. Acad. Sci. USA* 88:9979–9983 (1991).
El–Deiry, Wafik et al., "WAF1, a Potential Mediator of p53 Tumor Suppression." *Cell* 75:817–825 (1993).
Young, Robert L. and Korsmeyer, Stanley J., "A Negative Regulatory Element in the *bcl–2* 5'–Untranslated Region Inhibits Expression from an Upstream Promoter." *Mole. Cell. Biol.* 13:3686–3697 (1993).
Prives, Carol and Manfredi, James J. "The p53 Tumor Suppressor Protein: Meeting Review." *Genes and Development.* 7:529–534 (1993).
Miyashita, Toshiyuki et al., "Identification of a p53–dependent Negative Response Element in the BCL–2 Gene." *Cancer Res.* 54:3131–3135 (1994).
Miyashita, Toshiyuki et al., "Tumor Suppressor p53 is a Regulator of BCL–2 and BAX Gene Expression in Vitro and in Vivo." *Oncogene.* 9:1799–1805 (1994).
El–Deiry, Wafik S. et al., "Definition of a Consensus Binding Site for p53." *Nature Genetics.* 1:45–49 (1992).

*Primary Examiner*—Douglas W. Robinson
*Assistant Examiner*—Thanda Wai
*Attorney, Agent, or Firm*—Campbell & Flores LLP

[57] ABSTRACT

The present invention provides regulatory elements that are linked to genes involved in cell death. For example, the present invention provides a p53-RE$^D$, which is involved in p53-mediated down-regulation of the bcl-2 gene, and the bax promotor, which contains a p53-RE$^U$ that is involved in p53-mediated up-regulation of the bax gene. The invention also provides screening assays for identifying agents such as drugs that effectively modulate expression of a gene that is involved in cell death. In addition, the invention provides methods for modulating the level of apoptosis in a cell.

6 Claims, 8 Drawing Sheets

```
GTAGACTGAT   ATTAACAATA   CTTACTAATA   ATAACGTGCC   TCATGAAATA
AAGATCCGAA   AGGAATTGGA   ATAAAAATTT   CCTGCGTCTC   ATGCCAAGAG
GGAAACACCA   GAATCAAGTG   TTCCGCGTGA   TTGAAGACAC   CCCCTCGTCC
AAGAATGCAA   AGCACATCCA   ATAAAATAGC   TGGATTATAA
```

FIG. 1

```
                                  CC TGCTGATCTA TCAGCACAGA

TTAGTTTCTG CCACTTTTTA AACTTCATAT TCCTTTTCTT TTTACACAAA    -901

CACAAACATT CGAGTCATGA CTGGGTGGGG TGGCTCAAGC CTGTAATCTC

AGCACTTTGG GAGGCCAAGG TGCGAGGATG CTTGAGTCTG GGAGTTCAGA    -801

GACCAGCCTG GCAACATAG AGAGACCTCA TCTCCACATA AAAGTTTTA

AAAATTAACC AGGGGCGGTG TAGTCCCAGC TACTCAGGAG GCTGAGGTGG    -701

GAGGCTTCAG CCCGGGAATT CCAGACTGCA GTGAGCCATG ATTGGGCCAC

TGCACTCCAG CCTGGGCAAC ACAGTGAGAC CCTGTCTCAA AAAAAAAAA    -601

AAAAAAAAAA AAAAAACAG GAAAAAACAA ACAAACAGAA AAGCAGGCCT

GGCGCGGTAG CTCATGCCTG TAATCCCAGC GCTTTGGAAG GCTGAGACGG    -501

GGTTATCTCT TGGGCTCACA AGTTAGAGAC AAGCCTGGGC GTGGGCTATA

TTGCTAGATC CAGGTCTCTG CAAAAAACAA AACCACTCAG TTTTTAGTCA    -401

TCTATAACGT CCTGCCTGGA AGCATGCTAT TTTGGGCCTC TGAGCTTTTG

CACTTGCTAA TTCCTTCTGC GCTGGGGAGA GCTCAAACCC TGCCCGAAAC    -301

TTCTAAAAAT GGTGCCTGGA TAAATGAAGG CATTAGAGCT GCGATTGGAC

GGGCGGCTGT TGGACGGCGC CACTGCTGGN ACTTATCGGG AGATGCTCAT    -201

TGGACAGTCA CGTGACGGGA CCAAACCTCC CGAGGGAGCG AGGCAGGTGC

GGTCACGTGA CCCGGCGGCG CTGCGGGCA GCGGCCATTT TGCGGGGCGG    -101

CCACGTGAAG GACGCACGTT CAGCGGGGCT CTCACGTGAC CCGGGCGCGC

TGCGGCCGCC CGCGCGGACC CGGCGAGAGG CGGCGGCGGG AGCGGCGGTG     -1
```

FIG. 9

PROMOTORS THAT REGULATE THE EXPRESSION OF GENES INVOLVED IN CELL DEATH

This application is a continuation-in-part of United States Ser. No. 08/182,619, filed Jan. 14 1994, now U.S. Pat. No. 5,484,710.

This work was supported by grant CA60181 awarded by the National Cancer Institute. The United States Government has certain rights in this invention.

BACKGROUND OF THE INVENTION

1. Field of the Invention

This invention relates generally to the fields of molecular biology and gene regulation and more specifically to regulatory elements that are present in genes involved in cell death.

2. Background Information

Cell death occurs by a variety of processes including, for example, programmed cell death and necrosis. The term "apoptosis" describes the morphological features of cells undergoing the process of programmed cell death, which is responsible for maintaining a steady-state level of cells in a self-renewing tissues. Under normal conditions, apoptosis assures that the number of dying cells in a tissue is roughly equivalent to the number of newly produced cells. However, in various disease states or as a result of an insult to a tissue, dysregulation of the process of apoptosis can occur. Similarly, various diseases states are associated with increased levels of cell death due to processes other than apoptosis.

In Alzheimer's disease, Parkinson's disease, Huntington's chorea, epilepsy, amyotrophic lateral sclerosis, stroke, ischemic heart disease, spinal cord injury and many viral infections, for example, abnormally high levels of cell death occur. In at least some of these diseases, there is evidence that the excessive cell death occurs through mechanisms consistent with apoptosis. Among these are 1) spinal cord injury, where the severing of axons deprives neurons of neurotrophic factors necessary to sustain cellular viability; 2) stroke, where after an initial phase of necrotic cell death due to ischemia, the rupture of dead cells releases excitatory neurotransmitters such as glutamate and oxygen free radicals that stimulate apoptosis in neighboring healthy neurons; and 3) Human Immunodeficiency Virus (HIV) infection, which induces apoptosis of T-lymphocytes.

In contrast, the level of apoptosis is decreased in cancer cells, which allows the cancer cells to survive longer than their normal cell counterparts. As a result of the increased number of surviving cancer cells, the mass of a tumor can increase even if the doubling time of the cancer cells does not increase. Furthermore, the high level of expression in a cancer cell of the bcl-2 gene, which is involved in regulating apoptosis and, in some cases, necrotic cell death, renders the cancer cell relatively resistant to chemotherapeutic agents and to radiation therapy.

The molecular mechanisms that regulate cell death are not well understood. It is now becoming clear, however, that several proteins such as Bcl-2 and a Bcl-2-related protein, termed "Bax," have a central role in apoptosis. Specifically, the expression of Bcl-2 in a cell blocks apoptosis, whereas the expression of Bax in a cell induces apoptosis. Thus, when Bcl-2 levels in a cell are decreased and/or when Bax levels are elevated, the rate of cell death is accelerated. Conversely, when Bcl-2 levels in a cell are increased and/or when Bax levels are decreased, apoptosis is inhibited. In addition, Bcl-2 also may be involved in the process of necrotic cell death.

The p53 tumor suppressor protein (p53) is another example of a protein that is involved in the process of apoptosis. The wild-type p53 protein induces apoptosis in a cell, whereas mutant p53 proteins do not induce apoptosis. Many cancers have mutations in the genes encoding p53 and, therefore, either do not express any p53 protein or express a mutant p53 protein. Thus, the absence of a wild-type p53 tumor suppressor in a cancer cell also can contribute to the low level of apoptosis that occurs in cancer cells.

The ability to manipulate the mechanism by which the genes involved in cell death are regulated would provide physicians with a potential target for therapies aimed at ameliorating the effects of diseases that are characterized by abnormal levels of cell death and also would allow for the development of methods to identify agents that can effectively regulate, for example, apoptosis in a cell. However, the mechanisms by which these genes are regulated in a cell have not yet been described. Thus, there exists a need to identify methods to manipulate the regulatory elements for genes involved in apoptosis. The present invention satisfies this need and provides related advantages as well.

SUMMARY OF THE INVENTION

The present invention provides nucleotide sequences that are gene regulatory elements, which regulate the expression of genes involved in cell death. For example, the invention provides p53 responsive elements (p53-RE), such as the p53-RE$^D$, which down-regulates expression of the bcl-2 gene, and the p53-RE$^U$, which up-regulates expression of the bax gene. The invention also provides the bax promotor, which regulates expression of the bax gene or heterologous genes linked to the bax promotor. The invention further provides screening assays for identifying agents such as drugs that effectively modulate expression of a gene that contains a p53-RE or the bax promotor and is involved in cell death. The invention also provides methods for modulating the level of apoptosis in a cell.

BRIEF DESCRIPTION OF THE DRAWINGS

FIG. 1 shows the sequence for the p53-RE$^D$ element, which consists of sequence positions −273 to −84 of the bcl-2 gene (SEQ ID NO: 1).

FIG. 9 shows the nucleotide sequence of the human bax promotor (SEQ ID NO: 24). The approximate transcription start site is indicated by an arrow. The perfect (10/10 matches) p53 binding site consensus sequence is boxed and the three imperfect p53 binding sites are underlined or overlined with dashes. The TATAA box is double underlined and the CACGTG motifs are single underlined.

DETAILED DESCRIPTION OF THE INVENTION

Figure 2:
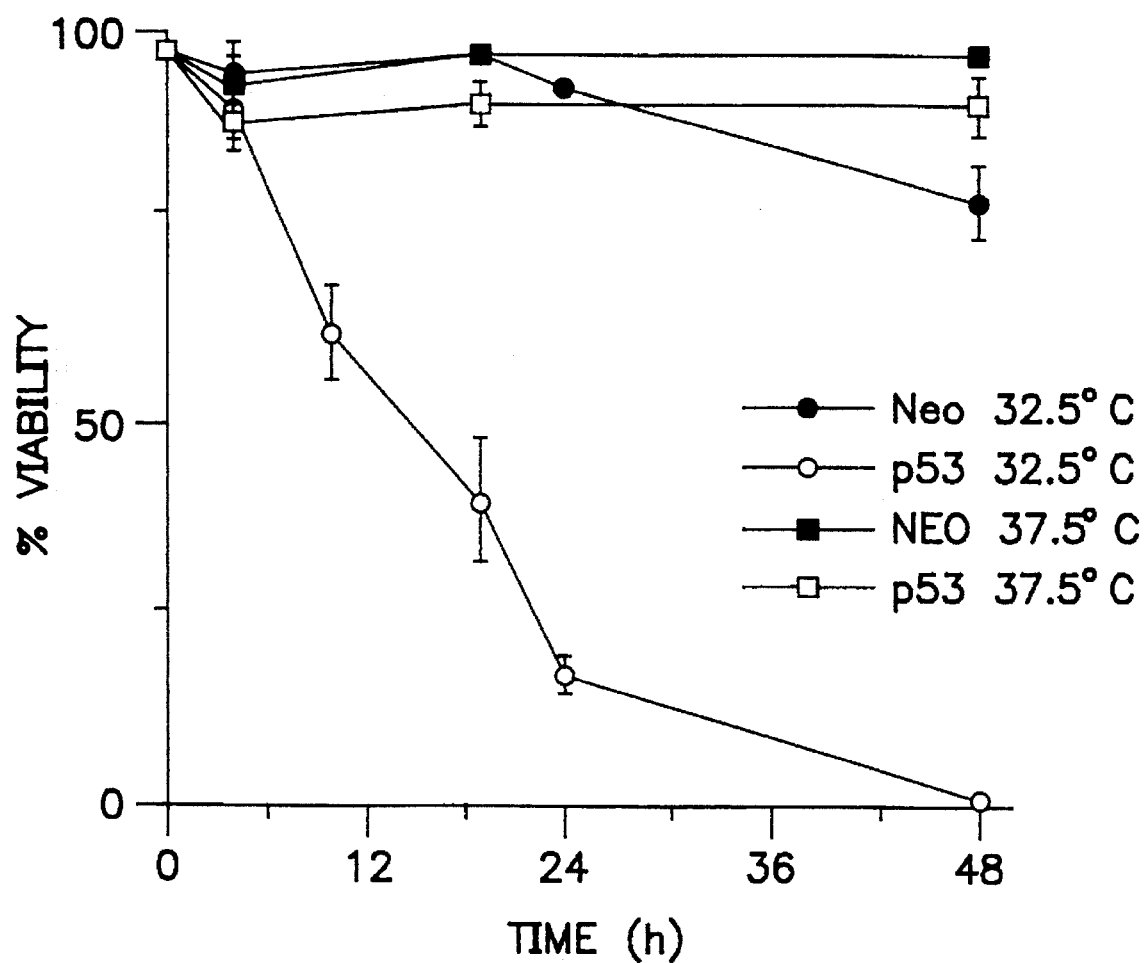
FIG. 2 demonstrates the effect of wild-type p53 tumor suppressor protein on cell survival. "p53" indicates cells transfected with a plasmid encoding a temperature-sensitive p53 protein and "Neo" indicates cells transfected with a control plasmid. Cell viability was determined using trypan blue and was examined at various times after shifting the cells to the permissive temperature (32.5° C.) or after incubating the cells at 37° C. Each point represents the mean ± standard deviation for three experiments.

The present invention provides nucleotide sequences that act as regulatory elements (also called "responsive elements") to control the expression of genes such as bcl-2 and bax, which are involved in the process of cell death (see Vaux et al., Nature 335:440–442 (1988); Oltvai et al., Cell 74:609–619 (1993); Kane et al., Science 262:1274–1277 (1993)). A regulatory element can be characterized, in part, by its being linked to a gene, the expression of which it regulates, and by its being activated due to binding or release of a trans-activating factor.

In one aspect, the present invention provides p53 responsive elements (p53-RE) and active fragments thereof, which are bound by the p53 tumor suppressor protein to regulate gene expression. For example, the present invention provides the p53-RE$^D$, which is required for p53-mediated down-regulation of the bcl-2 gene, and the p53-RE$^U$, which is required for p53-mediated up-regulation of the bax gene. FIG. 1 shows positions ⁻276 to ⁻84 of the bcl-2 gene (SEQ ID NO: 1), which confer the activity of a p53-RE$^D$ as defined herein. In addition, positions ⁻485 to ⁻449 of the bax promotor (SEQ ID NO: 27) confer the activity of a p53-RE$^U$ as defined herein (see FIG. 9).

One skilled in the art would recognize that the point mutations and deletions can be made to the p53-RE sequences disclosed herein without altering the ability of the sequence to act as a p53-RE. In addition, active fragments of a p53-RE can be obtained. For example, Example III.C. provides methods that demonstrate that various active fragments of a p53-RE$^U$ can be constructed and that such active fragments confer p53-mediated up-regulation of a heterologous gene. Similar methods can be used for identifying active fragments of the p53-RE$^D$ shown in FIG. 1. Other methods for identifying an active fragment of a p53-RE are routine and well known in the art. For example, overlapping fragments of a p53-RE as disclosed herein can be synthesized and cloned into the vectors described in Example II or Example III to determine active p53-RE$^D$ and p53-RE$^U$ fragments. Similarly, point mutations can be introduced into the disclosed p53-RE sequences using, for example, site-directed mutagenesis (see Example III.B.) or by synthesizing sequences having random nucleotides at one or more predetermined positions.

In some cases, a regulatory element can be characterized in that the binding of a protein other than or in addition to p53 is required for activity. The bax promoter, for example, as disclosed herein can bind p53 as well as other proteins such as the Myc protein (see FIG. 9). Thus, in another aspect, the invention provides the bax promotor and active fragments thereof, which regulate the expression of a gene involved in apoptosis.

The nucleotide sequence of a portion of the human bax promotor is shown in FIG. 9 (SEQ ID NO: 24). As used herein, the term "bax promotor" means the nucleotide sequence shown in FIG. 9 (SEQ ID NO: 24) or active fragments thereof, which can bind a protein and confer regulatory activity upon a gene. One skilled in the art would know methods such as those described in Example III for identifying active fragments of the bax promotor. For example, the p53-RE$^U$ located at positions ⁻485 to ⁻449 of the bax promotor (SEQ ID NO: 27) can bind wild-type p53 and up-regulate expression of a gene involved in apoptosis and, therefore, is an active fragment of the bax promotor. Other active fragments of the bax promotor such as the sequences shown as positions ⁻485 to ⁻465 (SEQ ID NO: 28) and positions ⁻474 to ⁻449 (SEQ ID NO: 29) also are disclosed herein (see, for example, FIG. 10).

The p53 tumor suppressor is a 53 kilodalton (kDa) nuclear phosphoprotein that can induce the transcription of various genes by binding to a consensus DNA binding site on the gene or can inhibit transcription by interacting, for example, with other transcription factors required for expression of a gene (Zhan et al., Mol. Cell. Biol. 13:4242–4250 (1993), which is incorporated herein by reference). The p53 protein contributes to tumor suppression through at least two mechanisms, arrest of cell proliferation and induction of apoptosis (see Hartwell, Cell 71:543–546 (1992); Yonish-Rouach et al., Nature 352:345–347 (1991); Baker et al., Science 249:912–915 (1990)). Recently, potential pathways to explain the mechanism by which p53 arrests cell proliferation have been suggested (Harper et al., Cell 75:805–816 (1993); El-Deiry et al., Cell 75:817–825 (1993)). However, the mechanism by which p53 induces apoptosis has not yet been described.

Various genes encoding proteins such as Bcl-2 and Bcl-2-related proteins such as Bax are involved in the process of cell death. As used herein, the term "cell death" is used in its broadest sense to include cell death resulting from various processes such as apoptosis and necrosis. Reference to "a gene involved in cell death" is meant to include a gene that encodes a protein required for the initiation or continuation of the process of cell death such as apoptosis, which occurs in many cell types as a result of development, damage or disease.

A gene involved in cell death can be characterized, for example, by containing a p53-RE having the characteristics described herein. Genes involved in apoptosis are well known in the art and include, for example, the bcl-2 gene and the bax gene. Genes encoding members of the Bcl-2-related family of proteins such as Bcl-X and genes encoding members of the family of Bcl-2-associated proteins such as R-ras (Fernandez-Sarabla and Bischoff, *Nature* 366:274–275 (1993), which is incorporated herein by reference) also are considered genes involved in apoptosis, provided that such a gene contains a p53-RE.

The terms "p53-responsive element" and "p53-RE" specifically refer to a cis-acting, position-independent DNA sequence that is required for regulation of a gene by the p53 tumor suppressor. As described below, the p53-RE is considered a cis-acting regulatory element because it must be linked to a gene in order to confer p53-mediated regulation upon the gene. In addition, the p53-RE is considered a position-independent element because it is active regardless of whether it is located upstream or downstream of the promotor of a gene involved in cell death (see Example II.C.). It follows from the characteristics of the p53-RE that the term "linked" is used in its broadest sense and indicates that the p53-RE and the gene are located within a continuous DNA sequence that usually does not exceed about ten to fifty kilobases (kb).

Regulation of a gene that is involved in cell death and contains a p53-RE is mediated by the p53 tumor suppressor. As used herein, the term "p53-mediated regulation" means that the wild-type p53 tumor suppressor protein is required for the regulation of gene expression by the p53-RE. As shown in Example I, expression of wild-type p53 tumor suppressor in a cell results, for example, in the down-regulation of bcl-2 in a cell, which, in turn, results in cell death (see, also, FIGS. 1–5).

p53-mediated regulation can be due to direct binding of the p53 tumor suppressor to the p53-RE or can be due to p53 interacting with one or more other proteins, any or all of which can bind to the p53-RE to cause regulation of the gene (see Example II.D.). A p53 binding site has been described in several genes that are induced by p53 (El-Deiry et al., supra, 1993; El-Deiry et al., *Nat. Genet.* 1:45–49 (1992), each of which is incorporated herein by reference).

A consensus p53 binding site consists of two or more of the 10 base pair (bp) sequence: 5'-Pu-Pu-Pu-C-(A/T)-(T/A)-G-Py-Py-Py-3' (SEQ ID NO: 30; "Pu" indicates purine and "Py" indicates a pyrimidine) separated by 0 to 13 bp (El-Deiry et al., supra, 1992). For convenience, the term "consensus p53 binding site" is used to refer to one 10 bp sequence shown as SEQ ID NO: 30. However, it should be recognized that, for p53 binding to occur, the binding site must consist of at least two of the 10 bp sequences shown as SEQ ID NO: 30. As used herein, reference to "a perfect match" of the consensus p53 binding site means a 10 bp sequence that contains a nucleotide sequence encompassed within the consensus sequence shown as SEQ ID NO: 30, whereas reference to "an imperfect" consensus p53 binding site means a 10 bp sequence wherein at least one nucleotide is different from the consensus sequence shown as SEQ ID NO: 30.

Inspection of the DNA sequence of the p53-RE$^D$ (SEQ ID NO: 1) does not reveal a consensus p53 binding site (FIG. 1; see, also, Young and Korsmeyer, *Mol. Cell. Biol.* 13:3686–3697 (1993), which is incorporated herein by reference). However, the p53-RE$^U$ shown at positions −485 to −449 of the bax promotor (SEQ ID NO: 27) contains one 10 bp sequence that is a perfect match of the consensus p53 binding site and three imperfect consensus p53 binding sites and can bind p53 (see FIGS. 9 to 11 and Example III). A p53-RE$^U$ also can consist of one perfect match of the consensus p53 binding site and at least one imperfect consensus p53 binding site (see, for example, FIG. 10).

p53 also has been reported to interact with other transcription factors such as the TATA-binding factor to cause down-regulation of a gene (see Zhan et al., 1993). A common feature of genes that are down-regulated by p53 is that the gene is expressed from a TATA-containing promotor. Although the bcl-2 gene contains a TATAA sequence, only minimal bcl-2 gene transcription occurs from this promotor. Instead, transcription of bcl-2 is initiated predominantly at a second, non-TATA-containing promotor. Thus, down-regulation of the bcl-2 gene by p53 is not likely the result of p53 binding to a TATA-binding transcription factor.

p53-mediated regulation results in activation of gene expression by a p53-RE. As used herein, the term "activation" indicates that the p53-RE is performing its normal function of regulating the expression of the gene to which the p53-RE is linked. For example, the function of a p53-RE such as the p53-RE$^D$ in the bcl-2 gene can be to down-regulate the expression of the gene. The term "down-regulated" indicates that expression of the gene is reduced or inhibited. A p53-RE having such characteristics is referred to as a "negative regulatory element," which, when activated, decreases the level of transcription of the gene to which it is linked.

Young and Korsmeyer (1993) have described a negative regulatory element that is contained within the same DNA sequence as the p53-RE$^D$ described herein. However, the element described by Young and Korsmeyer is a position-dependent regulatory element and, therefore, is readily distinguishable from the p53-RE$^D$, which is a position-independent element that can regulate expression of a gene whether the p53-RE$^D$ is located upstream or downstream of the gene (see Example II.B.).

Another p53-RE is the p53-RE$^U$ element, examples of which are disclosed, for example, in the −485 to −449 region of the bax promotor (SEQ ID NO: 27). In contrast to a p53-RE$^D$, a p53-RE$^U$ element functions as a positive regulatory element, which is an element that, when activated by p53, increases the level of transcription of the gene to which it is linked.

The identification of gene regulatory elements such as the p53-RE and the bax promotor allows manipulation of the mechanism by which cell death is regulated in diseases that are characterized by abnormal levels of cell death. As used herein, the term "disease characterized by an abnormal level of cell death" refers to diseases such as cancer, in which the level of apoptosis is less than normal for the particular cell-type from which the tumor cell is derived.

It is well known, for example, that the p53 tumor suppressor often is absent or mutated in cancer cells. As a result, bcl-2 gene expression can be improperly regulated in the p53-deficient cells, resulting in higher than normal levels of Bcl-2 protein, which decreases apoptosis in these cells. As used herein, the term "p53-deficient cell" is meant to include any cell that does not express a wild-type p53 tumor suppressor protein. Such a cell, for example, can be a p53-null cell, which is a cell that does not contain any p53 protein, or a cell that contains a mutant p53 protein. A cancer cell that has point mutations, allelic loss, rearrangements or deletions of both p53 genes and, therefore, either does not express a p53 protein or expresses a mutant p53 protein is an example of a p53-deficient cell. Other p53-deficient cells are known and include, for example, H358 lung cancer-derived cells and Saos-2 osteosarcoma cells, which are described in Examples II and III. Such cells are particularly useful for identifying agents that can effectively regulate cell death as described in detail below.

The importance of apoptosis regulation for in vivo suppression of tumor formation by p53 has been demonstrated in studies using transgenic mice. In these mice, tumor development was associated with the loss of p53 and was characterized by decreased rates of cell death rather than by increased rates of cell proliferation (Symonds et al., *Cell* 78:703–711 (1994)). Furthermore, the relative insensitivity of p53-deficient tumor cells to induction of apoptosis by chemotherapeutic drugs and radiation may be responsible for the clinical observation that patients having such tumors tend to have a worse prognosis as compared to patients having histologically similar tumors that contain normal p53 (see, for example, Thor et al., *J. Natl. Canc. Inst.* 84:845–855 (1992; Sun et al., *Lancet* 340:1369–1373 (1992)).

Other diseases such as stroke are characterized by abnormally high levels of cell death due to necrosis and apoptosis. In stroke, oxygen deprivation leads to necrotic cell death. Subsequent destruction of the necrotic neuronal cells results in the release of agents such as glutamate, which can induce apoptosis in surrounding cells presumably, in part, by allowing intracellular levels of active oxygen species to increase (Behl et al., *Biochem. Biophys. Res. Comm.* 197:949–956 (1993), which is incorporated herein by reference). Increasing the level of Bcl-2 protein in neuronal cells exposed to glutamate or to agents that induce high intracellular active oxygen concentrations greatly increases cell survival (Behl et al., 1993; Kane et al., 1993).

Alzheimer's disease, ataxia telangiectasia, Bloom's syndrome and progeria also are characterized by having abnormally high levels of cell death. Patients having these diseases are characterized by an accumulation of DNA damage due, for example, to oxidative damage or to defects in DNA repair. Cells from ataxia telangiectasia patients are highly susceptible to ultraviolet- and X-radiation, which damages DNA in the cells and induces apoptosis. Exposure of ataxia telangiectasia cells to radiation has been reported to result in increased expression of genes containing the consensus p53 binding site (Kastan et al., *Cell* 71:587–597 (1992), which is incorporated herein by reference). Similarly, the abnormalities in cell death regulation in ataxia telangiectasia patients can be due to a defect in p53-mediated regulation of a gene such as bcl-2 or bax through a p53-RE.

Expression of wild-type p53 in some p53-deficient tumor cell lines results in spontaneous cell death (see, for example, Yonish-Rouach et al., supra, 1991; Shaw et al., *Proc. Natl. Acad. Sci., USA* 89:4496–4499 (1992)). However, the restoration of p53 activity in other p53-deficient tumor cell lines is not sufficient to trigger apoptosis but can render cells relatively more sensitive to induction of apoptosis by radiation and DNA-damaging chemotherapeutic drugs (see, for example, Fisher *Cell* 539–542 (1994)). These results indicate that elements other than a p53-RE, alone, are involved in regulating expression of genes involved in apoptosis. In this regard, analysis of tissues from p53 "knock-out" mice demonstrated that Bax protein levels are markedly reduced in prostate epithelium, central and peripheral neurons and small intestine, but not in other tissues examined (Miyashita et al., *Oncogene* 9:1799–1805 (1994a), which is incorporated herein by reference). Thus, other cellular factors such as tissue-specific factors can be involved in influencing the extent to which p53 is required for bax expression in vivo.

The present invention provides the bax promotor as shown in FIG. 9 (SEQ ID NO: 24), which can regulate the expression of a gene involved in apoptosis (see Example III). As shown in FIG. 9, the bax promotor consists of about 972 nucleotides. A TATAA box is present at position ⁻398 to ⁻394 and a transcription start site was mapped by primer extension to be about 22 bp downstream of the TATAA box. Thus, the bax promotor as disclosed herein includes a 5'-untranslated region (5-UTR) of about 370 nucleotides.

In addition to the p53-RE$^U$, which is located at positions ⁻485 to ⁻449 (SEQ ID NO: 27), the bax promotor contains four CACGTG motifs located within the 5'-UTR. These hexameric elements represents a potential binding sites for several transcription factors, including Myc and its homologs (see, for example, Zervos et al., *Cell* 72:223–232 (1993); Ayer et al., *Cell* 72:211–222 (1993)) which is a ubiquitously-expressed transcription factor whose activity is controlled by redox mechanisms (Pognonec et al., *J. Biol. Chem.* 267:24563–24567 (1992)).

Myc is known to induce apoptosis, for example, in response to serum-deprivation in fibroblasts or antigen-receptor crosslinking in T cell hybridomas (see, for example, Asken et al., *Oncogene* 6:1915–1922 (1992)). The presence of Myc binding sites in the bax promotor indicates that Myc can be involved in regulating apoptosis by up-regulating bax gene expression. Methods as disclosed herein or otherwise known in the art can be used to readily identify Myc binding and regulation of the bax promotor. Such methods also can be used to identify other regulatory elements present in the bax promotor.

The ability to manipulate the regulatory elements involved in the abnormal regulation of cell death in various diseases and the availability of a variety of cell types from patients having such diseases allows for the identification of agents that can be used to effectively treat patients having these diseases. Thus, the invention also provides screening assays for identifying agents such as drugs that effectively modulate expression of a gene that is involved in cell death and contains a p53-RE, a bax promotor or an active fragment thereof.

As used herein, the term "agent" means a biological or chemical compound such as a simple or complex organic molecule, a peptide, a protein or an oligonucleotide. The screening assays described herein are particularly useful in that they can be automated, which allows for high throughput screening of randomly designed agents in order to identify those agents that effectively modulate the level of expression of gene that is involved in cell death. Thus, the screening assays provide a method for identifying an "effective agent," which can be used to modulate cell death in a cell in vitro or in a patient.

As used herein, the term "modulate" means that the effective agent can increase or decrease the level of expression of a gene that is involved in cell death and that contains a p53-RE, a bax promotor or an active fragment thereof. For example, an effective agent for treating a cancer cell would allow a p53-deficient cell to behave as if it expressed a wild-type p53 tumor suppressor and, therefore, would down-regulate a bcl-2 gene and up-regulate a bax gene, which, in turn, would increase the level of apoptosis in the cancer cell. Such an effective agent can act in various ways. For example, an effective agent that is a peptide or a protein can modulate bcl-2 gene expression by binding to a p53-RE$^D$ and down-regulating expression of the gene. Alternatively, the effective can agent can be a small organic molecule that affects the structure or binding ability of a mutant p53 protein such that the p53 binds to a p53-RE and modulates the expression of the gene involved in cell death.

The screening assays described in Example IV allow one skilled in the art to identify an effective agent. The cotransfection assay described in Example IV.A. is particularly useful for screening various agents because it provides a well-defined system containing, for example, a temperature-sensitive p53 tumor suppressor and a well defined p53-RE. Screening of agents at the non-permissive temperature can be used to identify an effective agent, which will modulate transcription from the p53-RE to the same extent as the p53 protein does when expressed at the permissive temperature. This system contains a well-defined standard with which to compare the screening results. The assay described in Example IV.B. provides the further advantage of using a cell line obtained, for example, from a cancer patient. This assay allows the identification of agents that are particularly effective at modulating the p53-mediated regulation of apoptosis for a specific patient.

An effective agent also can modulate the expression of a gene involved in cell death by reducing or inhibiting the p53-mediated regulation of the gene, thereby up-regulating, for example, a bcl-2 gene and down-regulating a bax gene. An example of such an effective agent is an oligonucleotide that has the structure of a p53-RE and, therefore, can bind free p53 in a cell, thus preventing p53 from regulating expression of the gene. Alternatively, an effective agent can bind to the binding site on either p53 or on the p53-RE and sterically inhibit binding of p53 to the p53-RE.

Example V provides various assays for identifying an agent that effectively inhibits the p53-mediated regulation of a gene involved in cell death. The gel shift assay is particularly useful because it does not require the use of living cells. Thus, this assay can be used as a primary method of screening for potentially effective agents, which can then be examined using the transfection methods described in Examples V.B. and V.C. Again, these transfection assays allow the identification of effective agents that, in this case, decrease cell death. One skilled in the art would recognize that the assays disclosed in Examples IV and V can be modified to identify effective agents that regulate expression from the bax promotor or an active fragment thereof.

Agents that effectively decrease the level of cell death are particularly useful for treating a patient having a disease characterized by abnormally high levels of apoptosis. In this case, the effective agent can be administered to the patient. The route of administration of an effective agent to a patient will depend on the location of the diseased cells or tissue. For example, a patient with a neurodegenerative disorder, viral encephalitis, stroke, spinal cord injury or hereditary disorders that involve neuronal cell death such as ataxia telangiectasia can be treated by intrathecal administration of an agent. In contrast, it may be advantageous to administer an effective agent intravenously to a cancer patient with metastatic disease. These and other methods of administration are well known in the art and are selected based on the requirements for a particular patient.

In addition to being suitable for developing high throughput assays for screening agents, the assays provide the additional advantage of allowing the identification of agents that effectively regulate a p53-RE, the bax promotor or an active fragment thereof, any of which can readily be inserted into the vectors described herein. Also, if desired, any of several different reporter genes can be used to detect regulation by an effective agent. As used herein, the term "reporter gene" means a gene that encodes a gene product that can be identified using simple, inexpensive methods. As described, below, the chloramphenicol acetyltransferase reporter gene can be used to determine the level of transcriptional activity due, for example, to p53-mediated regulation of a p53-RE. Other reporter genes such as luciferase also can be used in the disclosed assays. Such reporter genes are well known in the art and described, for example, by Sambrook et al. *(Molecular Cloning: A laboratory manual* (Cold Spring Harbor Laboratory Press 1989), which is incorporated herein by reference). The following examples are intended to illustrate but not limit the present invention.

EXAMPLE I

The p53 Tumor Suppressor Induces Apoptosis by Modulating the Level of Expression of Bcl-2 and Bax This example demonstrates that the p53 tumor suppressor acts as a transcription factor that decreases bcl-2 gene expression and increases bax gene expression, thereby inducing apoptosis in a cell.

A. Transfection of M1 cells with a plasmid encoding a temperature-sensitive p53 tumor suppressor Cells from the murine myeloid leukemic cell line, M1, which do not express either the p53 tumor suppressor protein or mRNA encoding p53 (Yonish-Rouach et al., 1991), were maintained in Dulbecco's Modified Eagle's Medium (DMEM) supplemented with 10% (vol/vol) heat-inactivated horse serum, 2 mM glutamine, 50 U/ml penicillin and 0.1 mg/ml of streptomycin. Cells were either transfected with pSV2-Neo, alone, or were cotransfected with pSV2-Neo and pLTRp53cGval135, which encodes the murine Val-135 mutant p53, (see Michalovitz et al., *Cell* 62:671–680 (1990), which is incorporated herein by reference). The p53 tumor suppressor encoded by the plasmid, pLTRp53cGval135, is a temperature-sensitive mutant that has normal p53 activity at the permissive temperature, 32.5° C., but is inactive at the non-permissive temperature, 37° C. Transfection was by electroporation using the BioRad Gene Pulser. A pulse (1.5 kV, 1 mF) was delivered to a 0.7 ml suspension containing 1.5×10$^7$ cells and 50 µg of linearized plasmid DNA.

Following transfection, the cells were transferred into 24 well tissue culture plates at a concentration of 5×10$^4$ cells per well and allowed to adjust to the culture medium. After 48 hr incubation, the medium was removed and replaced with fresh medium containing 400 µg/ml of geneticin (1 ml per well; GIBCO/BRL; Gaithersburg Md.). In the cotransfected cells, one drug resistant clone, designated M1-p53, that expressed the highest levels of p53 was selected and used for further experiments. In the parallel transfection, one cell line, designated M1-Neo, was selected and used as a control in further studies.

Effect of p53 tumor suppressor on cell survival

M1-p53 and M1-Neo cells were incubated at either 32.5° C. or 37.5° C. Cell samples were taken at various times and viability was determined by trypan-blue exclusion (mean ± standard deviation for three experiments). As shown in FIG.

2, shifting the M1-p53 cells to 32.5° C. (permissive temperature) resulted in cell death. In contrast, cell survival was unchanged in M1-p53 cells maintained at 37° C. (nonpermissive temperature) and in M1-Neo cells incubated at either 32.5° C. or at 37° C.

These results indicate that expression of the p53 tumor suppressor in a cell results in cell death. Since a large number of M1-p53 cells die following incubation for 19 hr at 32.5° C., prior to some experiments dead cells were removed by centrifugation in Histopaque™ (SIGMA) as described by manufacturer.

C. Effect of p53 tumor suppressor on Bcl-2 mRNA levels

Bcl-2 is known to be involved in the process of apoptosis in a cell. Since p53 can induce cell death, the effect of the p53 tumor suppressor on Bcl-2 mRNA expression was determined using the reverse transcriptase-polymerase chain reaction (RT-PCR) method. As a control, the level of β2-microglobulin mRNA was determined in each sample.

M1-p53 and M1-Neo were incubated at 32.5° C. or 37° C. for various times, then collected. In samples of M1-p53 cells harvested 19 hr after being shifted to 32.5° C., dead cells were removed by centrifugation in Histopaque™ (SIGMA). Total RNA was isolated using TRIzol™ reagent (GIBCO/BRL) as described by the manufacturer. Reverse transcription was used to produce cDNA from the total RNA. Five µg RNA was incubated in a 50 µl reaction volume containing 200 U Moloney Leukemia Virus Reverse Transcriptase (GIBCO/BRL), 4 µl random hexamer (62.5 $A_{260}$ U/ml), 10 mM dithiothreitol, 20 U RNAsin (Promega) and 1 mM each of dGTP, dATP, dTTP, dCTP in the reaction buffer provided by the manufacturer. Reactions were incubated at 37° C. and allowed to proceed for 1 hr.

The cDNA product was amplified using the PCR method. Ten µl of the cDNA product was resuspended in a 100 µl reaction volume containing 2.5 U Taq DNA polymerase (Perkin-Elmer-Cetus), 60 mM each of dGTP, dATP, dTTP and dCTP and 50 pmol each of the forward and reverse primers in the reaction buffer provided by the manufacturer (primers are described below). Amplification cycles consisted of 94° C. for 30 sec, 57° C. for 30 sec, 72° C. for 3 min. In order to obtain data within the linear range of the assay, each cDNA was amplified in serial cycles from 27 to 39 and 18 to 27 with increments of 3 cycles for bcl-2 and β2-microglobulin, respectively.

Following the PCR reaction, RT-PCR products were size-fractionated by electrophoresis in 3% agarose gels, then transferred to GeneScreen Plus™ nylon filters (NEN Research Products) using 0.4N NaOH and hybridized with labelled internal probes (described below). Approximately 0.1 µg internal probe was end-labelled using γ-$^{32}$P-ATP (3000 Ci/mmol; NEN) and 10 U T4 polynucleotide kinase. Radiolabelled oligomers were purified by Bio-Spin™ chromatography columns (BioRad). Hybridization was performed at 57° C. in a buffer containing 5× SSPE (1× SSPE =0.15M NaCl/0.01M NaH$_2$PO$_4$, pH 7.0/1 mM EDTA), 0.6% SDS, 50 mg/ml denatured salmon sperm DNA. Following hybridization, the filters were washed in 5× SSPE/0.1% SDS at 57° C. and exposed to Kodak XAR films (Eastman Kodak) at −70° C. with an intensifying screen.

Primers and internal probes used were as follows. Murine bcl-2 forward primer: 5'-TGCACCTGAGCGCCTTCAC-3' (SEQ ID NO: 2); bcl-2 reverse primer: 5'-TAGCTGATTCGACCATTTGCCTGA-3' (SEQ ID NO: 3); bcl-2 internal probe: 5'-CCAGGAGAAATCAAACAAAGG-3' (SEQ ID NO: 4); murine β2-microglobulin forward primer: 5'-ATGGCTCGCTCGGTGACCCTAG-3 (SEQ ID NO: 5);

β2-microglobulin reverse primer: 5'-TCATGATGCTTGATCACATGTCTCG-3' (SEQ ID NO: 6), β2-microglobulin internal probe: 5'-GCTACGTAACACAGTTCCAC-3 (SEQ ID NO: 7). Forward and reverse primers were designed to span exon-intron junctions and, therefore, do not amplify any genomic DNA that may contaminate the RNA samples. Expected sizes of the amplified products of bcl-2 and β2-microglobulin were 575 bp and 373 bp, respectively.

Figure 3:
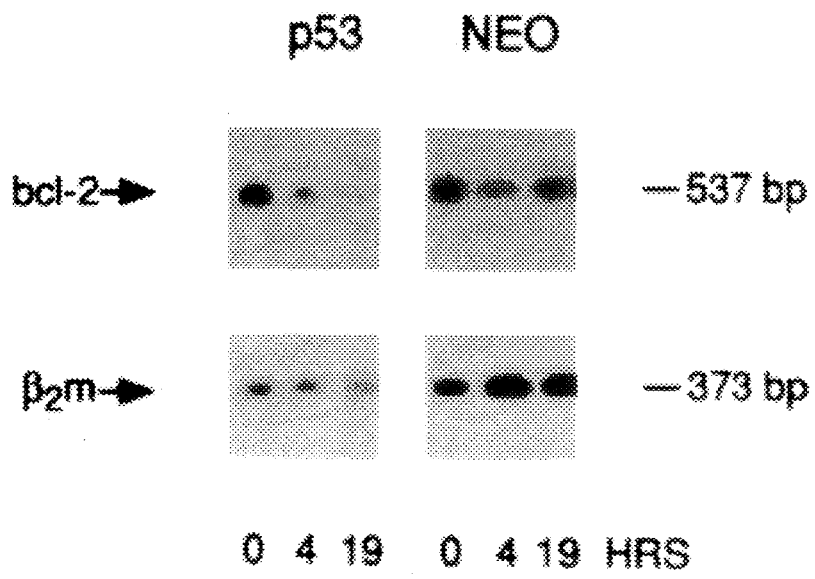
FIG. 3 shows the relative levels of Bcl-2 mRNA and β2-microglobulin (control) mRNA in cells cultured for 4 hr and 19 hr at 37° C. or 32.5° C. Cell lines are as described in FIG. 2. The mRNA levels were determined using the reverse transcriptase-polymerase chain reaction method.

As shown in FIG. 3, Bcl-2 mRNA levels decreased with time after M1-p53 cells were shifted to the permissive temperature (32.5° C.) and were less than 90% of the control level after 19 hr. In contrast, β2-microglobulin mRNA remained at the steady-state level during incubation at 32.5° C. In addition, Bcl-2 (and β2-microglobulin) mRNA levels remained at steady-state levels in M1-p53 cells maintained at 37° C. and in M1-Neo cells incubated at either 32.5° C. or at 37° C. These results indicate that the decrease in Bcl-2 mRNA in M1-p53 cells incubated at 32.5° C. is correlated to expression of the p53 tumor suppressor and is not due, for example, to the temperature of incubation.

D. Effect of p53 tumor suppressor on Bax mRNA levels

The product of the bax gene also is involved in the process of apoptosis in a cell. Therefore, the level of Bax mRNA expression was determined by northern blot analysis and compared to the level of expression of β2-microglobulin mRNA.

M1-p53 and M1-Neo were incubated at 32.5° C. or 37° C. for various times, then collected. In samples of M1-p53 cells harvested 19 hr after being shifted to 32.5° C., dead cells were removed by centrifugation in Histopaque™ (SIGMA). Total RNA was isolated as described above and 15 µg total RNA was size-fractionated in 1.2% agarose gels containing 2.2M formaldehyde (Sambrook et al., 1989). RNA was transferred to GeneScreen Plus™ nylon filters (NEN) using 10× SSC (1× SSC=0.15M NaCl/0.015M sodium citrate) and covalently bound to the membrane using UV irradiation. Probes, as described below, were labelled using α-$^{32}$P-dCTP by the random primer method (Sambrook et al., 1989; specific activity=1×10$^9$ cpm/µg).

$^{32}$P-labelled probes were added to the hybridization solution and hybridization was performed for 16 hr at 42° C. (hybridization solution is 50% formamide, 10% dextran sulfate, 1M NaCl, 1% SDS, 1× Denhardt's solution, 25 mM Tris (pH 7.4) and 50 mg/ml denatured salmon sperm DNA) (50× Denhardt's solution contains 5 g Ficoll (Type 400; Pharmacia), 5 g polyvinylpyrrolidone, 5 g bovine serum albumin (Fraction V; Sigma) and water to 500 ml). Following hybridization, the filters were washed with 2× SSC/0.1% SDS at room temperature, then with the same solution at 68° C. and exposed to X-ray film as described above.

A murine bax-specific probe was prepared by amplifying the entire open reading frame of the bax cDNA using RT-PCR as described above. The forward primer was 5'-GGAATTCGCGGTGATGGACGGGTCCGG-3' (SEQ ID NO: 8) and the reverse primer was 5'-GGAATTCTCAGCCCATCTTCTTCCAGA-3' (SEQ ID NO: 9). An Eco RI linker sequence was included at the 5'-end of each primer (underlined). Amplified cDNA products were gel-purified using GeneClean II™ (Bio 101, Inc.), cleaved using Eco RI (10 U/µg DNA) and subcloned into a Bluescript plasmid pSK-II (Stratagene). An Eco RI restriction fragment of approximately 600 base pairs was excised from the cloned insert, gel-purified and used as a hybridization probe. The murine β2-microglobulin cDNA probe is described by Parnes et al., Proc. Natl. Acad. Sci., USA 78:2253–2257 (1081), which is incorporated herein by reference.

Figure 4:
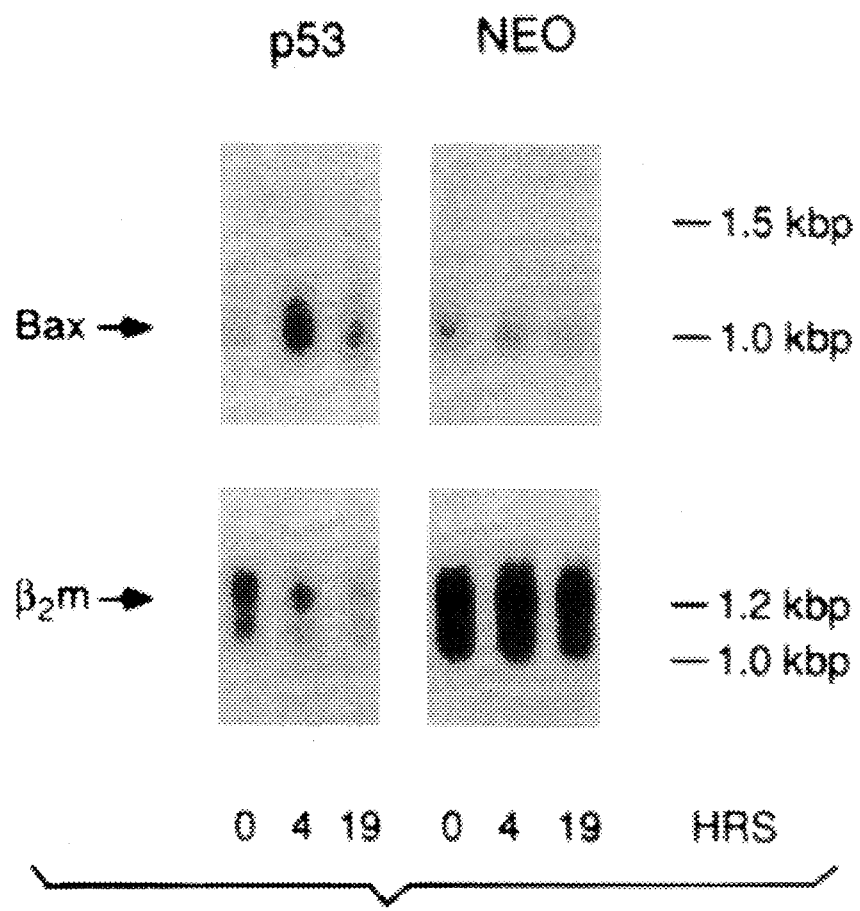
FIG. 4 shows a northern blot analysis of Bax mRNA and β2-microglobulin (control) mRNA obtained from cells incubated for 4 hr and 19 hr at 37° C. or 32.5° C. Cell lines are as described in FIG. 2.

As shown in FIG. 4, shifting M1-p53 cells to the permissive temperature resulted in a rapid increase in the level of Bax mRNA. No change in Bax mRNA levels were observed in M1-p53 cells maintained at 37° C. or in M1-Neo cells incubated at either 32.5° C. or at 37° C. Levels of β2-microglobulin mRNA did not change in any of the samples. These results indicate that the p53 tumor suppressor increases the expression of Bax mRNA. Thus, the p53 tumor suppressor regulates the expression of at least two genes involved in cell death, i.e., bcl-2 and bax.

E. Effect of p53 tumor suppressor on Bcl-2 and Bax protein levels

Decreased levels of Bcl-2 protein and increased levels of Bax protein induce apoptosis in a cell. In order to confirm that the mRNA changes described above are responsible for the Bcl-2 and Bax protein levels associated with apoptosis, the level of these proteins was determined.

M1-p53 and M1-Neo were incubated at 32.5° C. or 37° C. for various times, then collected. In samples of M1-p53 cells harvested 19 hr after being shifted to 32.5° C., dead cells were removed by centrifugation in Histopaque™ (SIGMA). Cells were washed in ice cold phosphate-buffered saline (PBS; pH 7.4) and collected by centrifugation. The cell pellets were resuspended in ice-cold lysis buffer containing the protease inhibitors, 0.7 mg/ml pepstatin, 1 mM phenylmethylsulfonylfluoride (PMSF), 0.23 U/ml aprotinin, 10 mM leupeptin and 1 mM benzamidine (lysis buffer is 10 mM Tris (pH7.4), 0.15M NaCl, 5 mM EDTA, 1% (v/v) Triton X-100). Following incubation on ice for 30 min, samples were centrifuged at 16,000× g for 10 min and the postnuclear supernatants were collected. Protein concentrations were determined using the bicinchoninic acid protein assay kit (Pierce, Inc.).

Twenty µg protein were size-fractionated under reducing conditions by sodium dodecyl sulfate-polyacrylamide gel electrophoresis (SDS-PAGE) using 12% gels, as described by Laemmli et al. (*Nature* 227:680–685 (1970), which is incorporated herein by reference), then electrophoretically transferred to nitrocellulose filters. The filters were incubated for 2 hr at room temperature with preblocking solution (10 mM Tris (pH 7.6), 0.15M NaCl, 5% skim milk, 2% BSA and 0.1% Tween 20), then the solution was removed, fresh solution containing 0.1–0.2% (vol:vol) of the appropriate antibody (described below) was added and incubation was continued for 16 hr at 4° C.

Following incubation with the first antibodies, the filters were washed 3× (5 min each) in a solution containing 0.12M NaCl, 8.7 mM NaH$_2$PO$_4$, 31 mM K$_2$HPO$_4$ (pH 7.6), then incubated with preblocking solution for 30 min, followed by fresh preblocking solution containing biotinylated goat anti-rabbit IgG (H+L) antibody (Vector Laboratories, Inc.). After washing as above, antibody binding was detected using an avidin-biotin-complex method, which employed the Vectastain ABC kit (Vector Laboratories Inc.) followed by the addition of 0.4 mg/ml AEC (3-amino-9-ethyl carbazole) containing 0.01% H$_2$O$_2$ for color development.

Rabbit anti-mouse Bcl-2 antibody was raised against synthetic peptides corresponding to amino acids 68 to 86 of the mouse Bcl-2 protein, including an additional cysteine at the C-terminus (RTSPLRPLVATAGPALSPVC; SEQ ID NO: 10), conjugated to maleimide-activated Keyhole Limpet Hemocyanin (Pierce, Inc., Rockford Ill.). Rabbit anti-mouse Bax antibody was raised against synthetic peptides corresponding to amino acids 43 to 61 of the mouse Bax protein, including an additional cysteine at the N-terminus (CPELTLEQPPQDASTKKLSE; SEQ ID NO: 11), conjugated to maleimide-activated Keyhole Limpet Hemocyanin.

Figure 5:
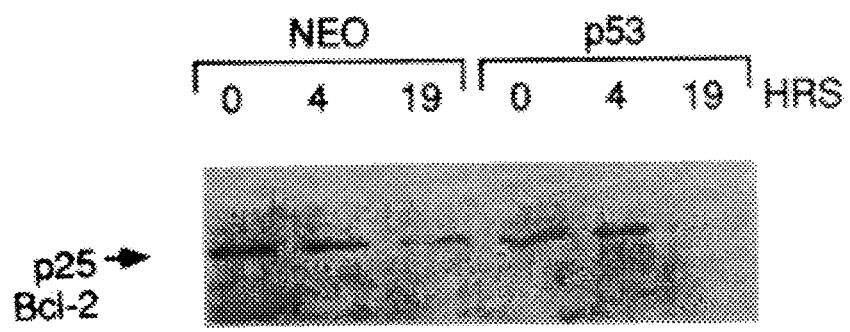
FIG. 5 shows an immunoblot analysis of the levels of Bcl-2 protein in cells incubated for 4 hr and 19 hr at 32.5° C. Cell lines are as described in FIG. 2.

As shown in FIG. 5, the steady-state level of p25-Bcl-2 protein declined in M1-p53 cells following 19 hr incubation at 32.5° C., but not in any of the control cells. Although Bcl-2 mRNA levels rapidly decline following transfer to the permissive temperature, no change in the p25-Bcl-2 protein was observed after 4 hr. However, this slower decline in the level of Bcl-2 protein likely reflects a relatively long half-life for the murine Bcl-2 protein. For comparison, the half-life of human Bcl-2 protein is about 10–12 hr (not shown).

Figure 6:
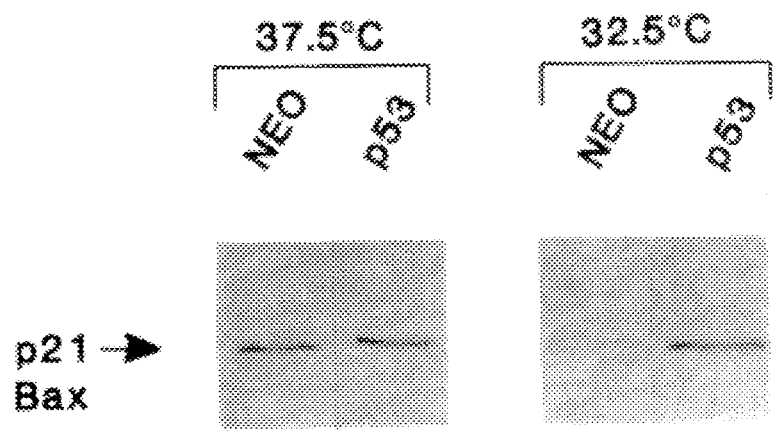
FIG. 6 shows an immunoblot analysis of the levels of Bax protein in cells incubated for 19 hr at 32.5° C. or 37° C. Cell lines are as described in FIG. 2.

In contrast to the result observed for the p25-Bcl-2 protein, the steady-state level of the p20-Bax protein increased following the shift of M1-p53 cells to the permissive temperature (FIG. 6). These results indicate that the induction of apoptosis by the p53 tumor suppressor is achieved by p53-regulation of the transcriptional activity of at least two genes involved in apoptosis. Furthermore, the magnitude of the effects shown here likely are an underestimate of the actual changes in the level of expression of bcl-2 and bax, since cells with low Bcl-2 and high Bax levels undergo apoptosis and, therefore, would have been lost from the population of cells analyzed in these experiments.

EXAMPLE II

Identification of the p53-Responsive Element that Down-Regulates bcl-2 Gene Expression (p53-RE$^D$)

This example demonstrates that a nucleotide sequence located in the 5'-untranslated region of the bcl-2 gene is required for transcriptional regulation of the bcl-2 gene by the p53 tumor suppressor.

A. Plasmid constructions

The nucleic acid sequence corresponding to positions −273 and −84 (p53-RE$^D$) of the bcl-2 gene was used in these studies (FIG. 1; SEQ ID NO: 1). This sequence does not contain a consensus p53 binding site (see El-Deiry et al., supra, (1993), which is incorporated herein by reference), but does contain a position-specific negative regulatory element that blocks bcl-2 gene expression (Young and Korsmeyer, supra, 1993).

The p53-RE$^D$ sequence was amplified with Pfu DNA polymerase (Stratagene) using the forward primer, 5'-GCGAAGCTTGTAGACTGATATTAAC-3' (SEQ ID NO: 12), and the reverse primer, 5'-GCGAAGCTTATAATCCAGCTATTTT-3' (SEQ ID NO: 13). A Hind III linker sequence was added to 5' end of each primer (underlined). Plasmid p18–21H was used as the template (Tsujimoto et al., *Proc. Natl. Acad. Sci., USA* 84:1329–1331 (1987), which is incorporated herein by reference).

The amplified p53-RE$^D$ product was gel-purified, then digested with Hind III and subcloned into the unique Hind III site of either pUCSV0CAT, which contains a chloramphenicol acetyltransferase (CAT) reporter gene, or pUCSV3CAT, which contains the CAT reporter gene and an SV40 promotor (Fukamizu et al., *Biomed. Biochim. Acta* 50:659–663 (1991), which is incorporated herein by reference). The Hind III site is located upstream of the CAT gene in pUCSV0CAT and between the SV40 promotor and the CAT gene in pUCSV3CAT; the constructed plasmids, therefore, were designated pUCSV40(p53-RE$^D$)CAT and pUC(p53-RE$^D$)CAT, respectively. Proper construction of the plasmids was confirmed by DNA sequencing.

The p53-RE$^D$ fragment also was subcloned in a position upstream or downstream of the SV40-CAT transcriptional unit in pUCSV3CAT. Essentially, the unique Hind III site was destroyed by digesting the plasmid with Hind III, then blunting the ends with the Klenow fragment of DNA polymerase I and self-ligating the plasmids. The BamHI site, which is located downstream of the CAT gene, and a Bgl II site, which is located upstream of the SV40 promotor then were converted to Hind III sites using the appropriate linkers. The pS3-RE$^D$ fragment was subcloned into each of the newly created Hind III sites to generate the plasmids, pSV40CAT(p53-RE$^D$) and p(p53-RE$^D$)SV40CAT, respectively.

The p53 expression plasmids, CMV-p53$_{wt}$ and CMV-p53$_{179}$, and the reporter plasmid, pFSVCAT, which contains six copies of the consensus p53 binding sequence and is regulated by p53 tumor suppressor, are described by Mietz et al., EMBO J. 11:5013–5020 (1992) and by Unger et al., EMBO J. 11:1383–1390 (1992), each of which is incorporated herein by reference. The plasmid, pCMVβ-Gal, which expresses B-gal and is not regulated by p53, was used as a control for transfection (MacGregor and Caskey, Nucl. Acids Res. 17:2365 (1989), which is incorporated herein by reference).

The p53-RE$^D$ is a position-independent negative regulatory element

Transient transfection assays were used to determine that the p53-RE$^D$ is a position-independent cis-acting regulatory element that can mediate p53-dependent inhibition of bcl-2 gene expression. Transient transfection assays were performed using human lung cancer-derived H358 cells, which have a homozygous deletion of p53 genomic DNA sequences and do not produce any detectable p53 mRNA or protein (p53-null) (Takahashi et al., Science 248:491–494 (1989), which is incorporated herein by reference).

H358 cells were maintained in RPMI 1640 medium supplemented with 10% (vol/vol) heat-inactivated fetal bovine serum (FBS), 2 mM glutamine, 50 U/ml penicillin and 0.1 mg/ml of streptomycin. Cells were plated in 6-well plates and were transfected when they reached about 70% confluency. Each well received 3 μg either CMV-p53$_{wt}$ or CMV-p53$_{179}$, 3 μg pFSVCAT, 1 μg pCMVβ-Gal and 30 μg of Lipofectin™ reagent (GIBCO/BRL) in 2.5 ml of HL-1™ medium (Ventrex).

Sixteen hr after transfection, the medium was replaced with fresh medium as described above and 32 hr later (48 hr after transfection) cells were collected by scraping with a rubber policeman into Hank's balanced salt solution (HBSS). The cells were washed 2× with HBSS, then the cell pellets were resuspended in 100 ml of ice cold 0.25M Tris (pH 7.8) and frozen and thawed 3× in ethanol-dry ice. Samples were centrifuged at 16,000× g for 5 min and the supernatants were collected.

CAT assays were performed by adding 30 μl of the cell lysate supernatant to a 70 μl reaction mixture containing 10 mM HCl, 43 mM acetyl-coenzyme A, 0.2 mCi (acetyl-$^3$H)-coenzyme A (4.48 Ci/mmol NEN) and 0.7 mM chloramphenicol in a 96-well plate and incubating at 37° C. for 1 hour. The reaction was stopped by adding 100 μl of 7M urea, the reaction mixtures were transferred to scintillation vials containing 2 ml of toluene scintillator and radioactivity was measured using a scintillation counter as described by Phahl et al., Meth. Enzymol. 189:267–270 (1990), which is incorporated herein by reference.

β-gal assays were performed by adding 10 μl of the cell lysate supernatant to a 190 μl reaction mixture containing 0.35% of 2-mercaptoethanol and 0.7 mg/ml of o-nitrophenyl-β-D-galactopyranoside in a 96-well plate and incubating at 37° C. for 30–60 min. β-gal activity was measured using an ELISA plate reader at a wavelength of 405 nm as described by Phahl et al. (1990).

For CAT assays and β-gal assays, serial dilutions of standard enzyme were included to verify that the results were within the linear phase of the reactions. In some experiments, the volume of the cell lysate supernatant added to the reaction was adjusted to obtain results within the linear range. Since p53 does not affect β-gal expression from pCMVβ-gal, CAT activity was normalized for β-gal activity. Normalization for protein concentration yielded comparable results (not shown).

Figure 7:
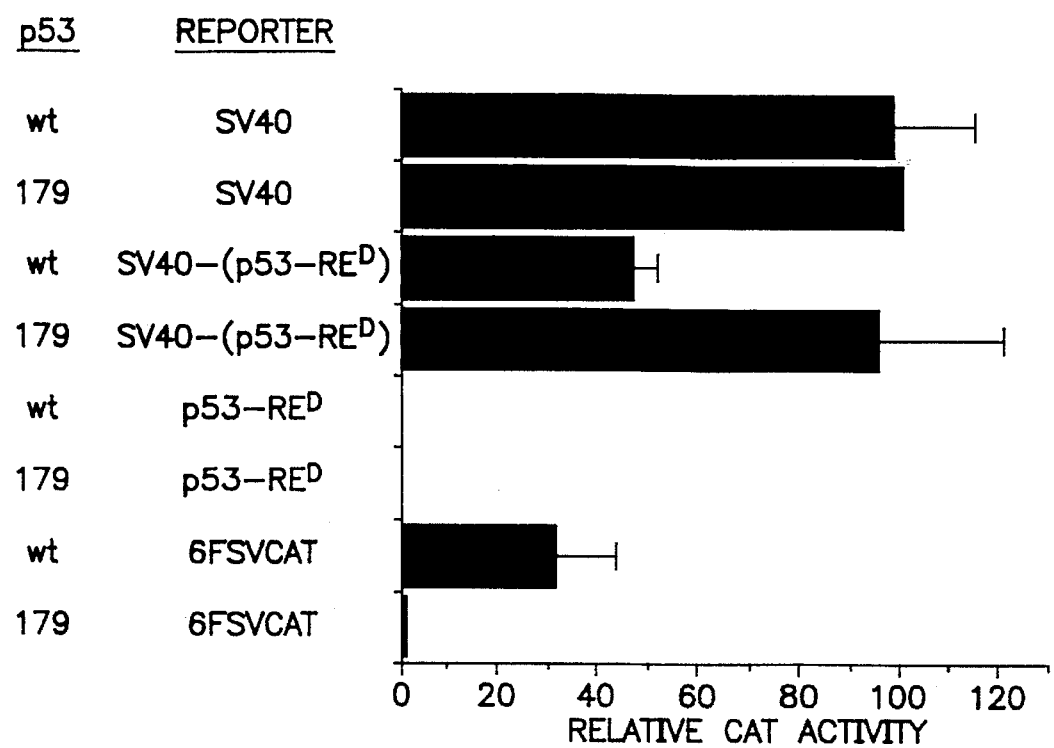
FIG. 7 provides the results of CAT assays used to identify the bcl-2 p53-RE$^D$. The various plasmids are described in detail in Example II.A. CAT activity was determined 48 hr after transfection and the results are expressed relative to the activity produced by the control pSVCAT construct, which does not contain a p53-RE$^D$.

As shown in FIG. 7, wild-type p53 tumor suppressor inhibited the expression of CAT activity from the pUCSV40 (p53-RE$^D$)CAT construct by about 50%, whereas the mutant p53$^{179}$ did not affect the level of expression of CAT from this plasmid. In contrast, wild-type p53 had no effect on the expression of CAT from pSV40CAT. No CAT activity was expressed from the plasmid, pUC(p53-RE$^D$)CAT, indicating that the p53-RE$^D$ does not have transcriptional activity, itself. CAT activity was present in cells that expressed wild-type p53 and contained the plasmid, pFSVCAT, indicating that p53 does not cause a general decrease in gene expression in H358 cells. These results indicate that expression of CAT activity in a cell can be inhibited by linking the p53-RE$^D$ to the CAT coding sequence and expressing wild-type p53 in the p53-null cells.

Figure 8:
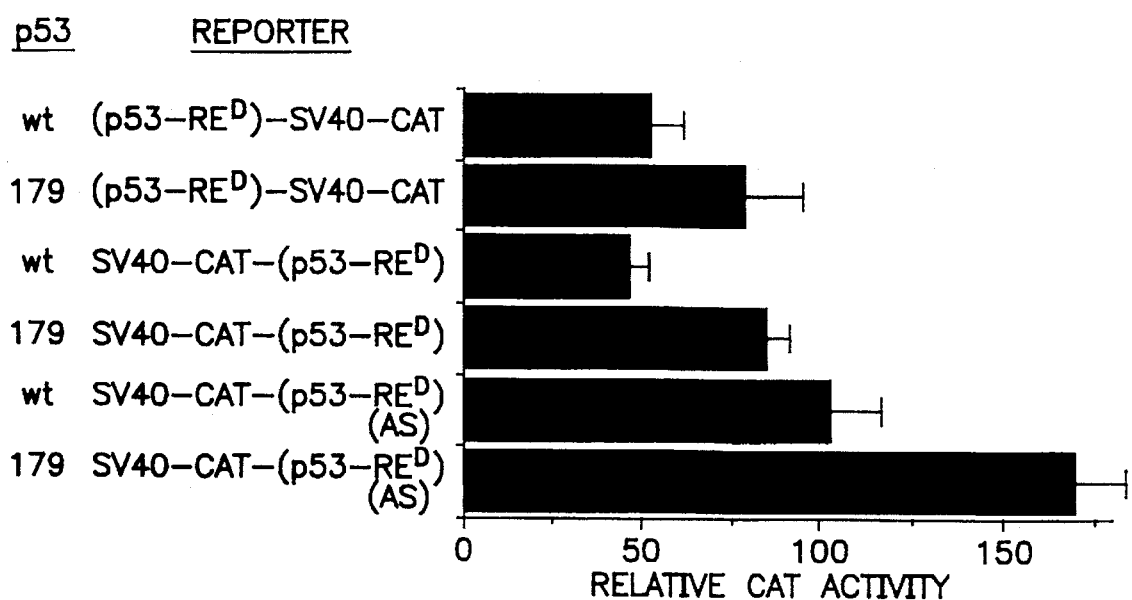
FIG. 8 provides the results of CAT assays used to determine the position specificity of the bcl-2 p53-RE$^D$. The plasmids are described in Example II.A. and relative CAT activity was determined as described in FIG. 7.

Expression from the pSV40(p53-RED)CAT plasmid produces a p53-RE$^D$-CAT fusion transcript. As a result, some type of post-translational mechanism of regulation could account for the decreased level of CAT activity in cells containing that plasmid. However, inhibition of CAT activity also was observed when wild-type p53 (as compared to mutant p53$^{179}$) was expressed in cells containing either pSV40CAT(p53-RE$^D$) or p(p53-RE$^D$)SV40CAT, which contain the p53-RE$^D$ in the upstream or downstream, respectively, of the SV40CAT transcription unit (FIG. 8).

These results demonstrate that the p53-RE$^D$ is a negative regulatory element that, in the presence of p53 tumor suppressor, acts at the transcriptional level to decrease the level of expression of a gene. In addition, the p53-RE$^D$ acts in a position-independent manner and, therefore, can be distinguished from the negative regulatory element described by Young and Korsmeyer (1993). Remarkably, the p53-RE$^D$ does not contain a consensus p53 binding site (El-Deiry et al., supra, 1993).

C. The p53 tumor suppressor binds the p53-RE$^D$

H358 cells were grown in T75 flasks and transfected with pCMV-p53$_{wt}$ or pCMV-p53$_{179}$ as described above. Untransfected cells were used as a negative control. Flasks were washed 3× with Tris-buffered saline, then 2.5 ml lysis buffer was added to each flask (lysis buffer is 20 mM HEPES (pH 7.6), 20% glycerol, 10 mM NaCl, 1.5 mM MgCl$_2$, 0.2 mM EDTA, 0.1% Triton X-100, 1 mM dithiothreitol (DTT), 1 mM PMSF, 10 μg/ml leupeptin, 10 g/ml pepstatin and 100 μg/ml aprotinin). Cells were dislodged by scraping and were pelleted by centrifugation at 2000 rpm at 4 ° C. Nuclei were resuspended at 2.5×10$^7$ nuclei per ml in nuclear extraction buffer, which is lysis buffer containing 500 mM NaCl. Nuclei were rocked gently for 1 hr at 4° C., then centrifuged for 10 min at 10,000 rpm. The supernatant was aliquoted into cryotubes, then quick frozen in liquid nitrogen and stored at −80° C.

Binding reactions were performed by adding 2 μl poly dI-dC (1 mg/ml; Pharmacia), 16 μl binding buffer, 1 1 (α-$^{32}$P)dCTP-labelled p53-RE$^D$ probe (1×10$^4$ cpm) and 1 μl unlabelled competitor p53-RE$^D$ DNA (3 pmol) to 2 μl of nuclear extract and incubating the reaction for 30 min at room temperature (binding buffer is 25 mM HEPES (pH 7.9), 0.5 mM EDTA (pH 8.0), 50 mM KCl, 10% glycerol, 0.5 mM DTT and 0.5 mM PMSF). In some experiments, 1 µg of an anti-p53 monoclonal antibody was included in the reaction mixture.

The p53-RE$^D$ probe was isolated by Hind III digestion of pUCSV40 (p53-RE$^D$)CAT, followed by gel purification of the p53-RE$^D$ fragment. The probe was labelled using ($\alpha$-$^{32}$P)dCTP and the Klenow fragment of DNA polymerase I (Sambrook et al., supra, 1989). Following the binding reaction, samples were subjected to polyacrylamide gel electrophoresis using a 4% gel and a buffer containing 50 mM Tris (pH 8.5), 0.4M glycine, 2 mM EDTA and 3% glycerol. The gels then were dried and exposed to X-ray film as described above.

The use of cell lysates prepared from p53$_{wt}$-producing cells results in a shift in the mobility of the $^{32}$P-labelled p53-RE$^D$, whereas cell lysates prepared from cells producing p53$^{179}$ do not shift the mobility of the probe. Additionally, the anti-p53 monoclonal antibody "supershifts" the probe. These results indicate that wild-type p53, but not mutant p53$^{179}$, binds to the p53-RE$^D$.

EXAMPLE III

Characterization of the bax promotor and p53-RE$^U$

This example describes a method for identifying and characterizing the bax promotor and the p53-RE$^U$, which is a DNA regulatory element that can bind p53 and up-regulate the expression of the bax gene.

A. Library screening

This section describes the construction and screening of a human genomic DNA library.

A human placental DNA library was cloned into the cosmid vector pWE15 (Stratagene, Inc.; San Diego Calif.) and was screened by a colony hybridization procedure using Biodyne nylon membranes (Pall Support Division; East Hills NY) and a 32P-labelled mouse bax cDNA (Miyashita et al., supra, 1994a). Filters were hybridized for 16 hr at 65° C. with 10$^6$ cpm/ml bax cDNA probe in 6× SSC containing 0.5% SDS, 5× Denhardt's solution and 100 µg denatured salmon sperm DNA. Following hybridization, filters were washed in 2× SSC/0.1% SDS, twice at 25° C., then once at 65° C.

Approximately 4×10$^5$ colonies were screened. Positive colonies were selected and rescreened. After three rounds of screening, 8 colonies remained positive. The cloned DNA in the positive colonies was examined by restriction endonuclease mapping and found to represent three independent, overlapping genomic clones that contained the entire bax gene. The plasmids containing the cloned genomic DNA were designated pTM597-1, 2, and 4.

pTM597-2 was digested with Bam HI to produce one 4 kb and two 3 kb fragments, which were subcloned into Bluescript pSKII (Stratagene, Inc.) to generate the plasmids pTM604-4, 6 and 7, respectively. The DNA sequence was determined for 972 nucleotides upstream of the translation start site. This 972 nucleotide sequence corresponds to the bax promotor and 5'-untranslated region (5'-UTR) of the bax gene (FIG. 9) and is referred to generally as the bax promotor.

A TATAA box is located 398 bp upstream from the open reading frame in the human bax gene. A transcription start site was mapped by primer extension to a position approximately 22 bp downstream of the TATAA box. Thus, the 5'-UTR of the human bax gene is predicted to be about 370 bp in length (see FIG. 9).

The p53 binding site in human genomic DNA consists of two copies of the 10 bp motif 5'-Pu-Pu-Pu-C-(A/T)-(T/A)-G-Py-Py-Py-3' (SEQ ID NO: 30; Pu= purine; Py=pyrimidine) separated by 0 to 13 bp (El-Deiry et al., supra, (1992)). Inspection of the bax promotor revealed a perfect p53 binding site (10/10 matches with consensus sequence) and three imperfect p53 binding sites located upstream of the TATAA box at positions ⁻485 to ⁻449 (see FIG. 9).

In the bax promotor, the perfect 10 bp consensus site (⁻474 bp to ⁻465 bp) is flanked on the 5'-side by a sequence that shares 7 of 10 matches with the consensus sequence, including a stretch of 7 of 7 matches in the core of this motif (FIG. 9). This second potential p53 binding site is separated from the perfect site by a single nucleotide. On the 3'-side of the perfect consensus site are two additional imperfect 10 bp motifs that are separated from the perfect p53 binding site by 0 or 6 bp and have 7/10 or 8/10 matches, respectively, with the consensus sequence.

Also within the 5'-UTR of the bax promotor are four CACGTG motifs, which are potential binding sites for several transcription factors, including Myc, the Myc homologs Max, Mad and Mxi-1, USF, TFE3 and TFEB (see, for example, Zervos et al., supra, 1993; Gregor et al., *Genes Devel.* 1730–1740 (1990); Fisher et al., *Genes Devel.* 5:2342–2352 (1991)). No other homologies with known cis-acting elements were identified in the cloned bax promotor.

B. CAT reporter gene constructs

This section describes methods for making CAT reporter constructs containing various portions of the bax promotor.

A 371 bp SmaI-SacI fragment, representing positions ⁻687 bp to ⁻318 of the bax promotor (SEQ ID NO: 25), was obtained from pTM604-4 and subcloned by blunt-end ligation into the Kind III site of the promotorless CAT plasmid pUCSVOCAT (Fukamizu et al., supra, 1991) to produce pTM667-3. pTM604-4 contains a 4 kb Bam HI fragment that includes the upstream region of the bax gene as well as exon 1.

A 94 bp DdeI-DdeI fragment from pTM604-4, which contains positions ⁻508 to ⁻415 of the bax promotor (SEQ ID NO: 26), was subcloned by blunt-end ligation into the Bgl II site of the minimal promotor CAT reporter plasmid pA10-CATBS (Spalholz et al., *J. Virol.* 61:2128–2137 (1987), which is incorporated herein by reference) to produce the plasmid pTM672-6. pA10-CATBS contains an SV40 early-region promotor in which the enhancer is deleted.

Oligonucleotides having the sequences 5'-GATCTCACAAGTTAGAGACAAGCCTG-3'0 (SEQ ID NO: 14; oligomer A) and 5'-TCGACAGGCTTGTCTCTAACTTGTGA-3' (SEQ ID NO: 15; oligomer B), which correspond to positions ⁻485 to ⁻465 of bax, were annealed. The annealed DNA fragment, which has overhanging 5'-ends compatible with Bgl II and Sal I, was subcloned into the Bgl II and Sal I sites of pA10-CATBS to produce pTM672-14.

pTM672-18 was produced by annealing the oligonucleotides 5'-GATCGAGACCAAGCCTGGGCGTGGGCTATA TTG-3' (SEQ ID NO: 16; oligomer C) and 5'-TCGACAATATAGCCCACGCCCAGGCTTGTCTC-3' (SEQ ID NO: 17; oligomer D), which correspond to positions ⁻474 to ⁻449 of the bax promotor (SEQ ID NO: 29 ), and subcloning the annealed fragment into the Bgl II and Sal I sites of pA10-CATBS.

Oligomers A and D also were annealed, the overhanging 5'-ends were filled-in with Klenow fragment in the presence of all four deoxyribonucleotide triphosphates, the 5' ends were phosphorylated using T4 DNA kinase and ATP and the resulting fragment was subcloned by blunt-end ligation into the Bgl II site of pA10-CATBS to produce pTM686-4, which is a reporter construct containing positions ⁻485 to ⁻449 of the bax promotor (SEQ ID NO: 27).

A CAT construct containing mutations in the p53 binding site was made by introducing four nucleotide substitutions into the consensus p53 binding sequence. The 94 bp Dde I fragment was isolated and mutations were introduced by site-directed mutagenesis using a PCR overlap extension technique (Ho et al., *Gene* 77:51–59 (1989), which is incorporated herein by reference).

Oligonucleotide primers for site-directed mutagenesis were 5'-GAAGATCTGAGACGGGGTTATCTCTT-3' (SEQ ID NO: 18; Bgl II site underlined); 5'-CGCGTCGACTGAGTGGTTTTGTTTTTT-3' (SEQ ID NO: 19; Sal I site underlined); 5'-AAGTTAGAGATAATGCTGGGCGTAGG-3' (SEQ ID NO: 20); and 5'-CCTACGCCCAGCATTATCTCTAACTT-3' (SEQ ID NO: 21; mutations are indicated in bold). pTM604-4 was used as a template and amplification was performed using Pfu heat-stable DNA polymerase (Stratagene, Inc.) as suggested by the manufacturer. The PCR product was gel-purified, digested with Bgl II and Sal I and subcloned into the Bgl II and Sal I sites of pA10-CATBS to produce pTM688-2. The presence of the mutations was confirmed by DNA sequencing.

C. The bax promotor and p53-RE$^U$ up-regulate gene expression

This section describes methods for identifying portions of the bax promotor involved in p53-mediated gene regulation.

Cell lines were maintained between 10% and 90% confluence in medium containing 10% FBS, 1 mM L-glutamine, 100 u/ml penicillin-G and 50 μg/ml streptomycin at 37° C. in 5% $CO_2$/95% air. HeLa and Saos-2 cells were grown in DMEM; H358 and TSU-prl were grown in RPMI-1640 (Mediatech; Washington D.C.). Saos-2 cell cultures also were supplemented with 1 mM Na-pyruvate and 1× nonessential amino acids (Hazelton Biologics, Inc.; Lenexa Kans.).

Cells were grown to approximately 70% confluence in 6 well (35 mm) plates. Transfection was performed by adding 30 μg Lipofectin (GIBCO/BRL), 3 μg CAT reporter gene plasmid, 1 μg pCMVβ-Gal plasmid and 3 μg either pCMV-p53$_{wt}$, pCMV-p53$_{179}$ or pRc/CMV plasmid DNA for 16 hr, essentially as described by Miyashita et al. (*Canc. Res.* 54:3131–3135 (1994b), which is incorporated herein by reference). After 48 hr, transfected cells were washed in HBSS, resuspended in 50 μl 10.25M Tris, pH 7.8, subjected to 3 freeze-thaw cycles and centrifuged at 16,000× g for 5 min to obtain supernatants for measurements of CAT and β-gal activity as described above (see, also, Miyashita et al., supra, 1994b).

In initial experiments, plasmid pTM667-3, which contained nucleotides ⁻687 to ⁻318 of the bax promotor (SEQ ID NO: 25), including the TATAA box, transcription start site and the consensus p53 binding sites, inserted upstream of the CAT gene, was cotransfected into various p53-deficient human tumor cell lines with an expression plasmid encoding either wild-type p53 (pCMV-p53$_{wt}$), the mutant inactive form of p53$^{179}$ (pCMV-p53$_{179}$) or no p53 protein (pRc/CMV).

In H358 human lung cancer cells, co-transfection of pTM667-3 with pCMV-p53$_{wt}$ resulted in strong trans-activation of the bax promotor, with an approximately 60× increase in CAT activity compared to cells co-transfected with pCMV-p53$_{179}$ or pRc/CMV (not shown). Similar results were obtained with every other tumor line tested. For example, wild-type but not mutant p53$^{179}$ produced about a 30 fold increase in CAT activity in p53-deficient Saos-2 osteosarcoma cells containing pTM667-3. In addition, wild-type p53 expression resulted in trans-activation of pTM667-3 in HeLa cells, which have reduced p53 activity due, in part, to expression of the human papillomavirus E6 protein in these cells (Liang et al., *Oncogene* 8:2645–2652 (1993)), and in p53-deficient Tsu-prl prostate cancer cells (not shown). These results demonstrate that wild-type p53 can up-regulate gene expression from the bax promotor in a variety of types of human tumor cell lines.

Figure 10:
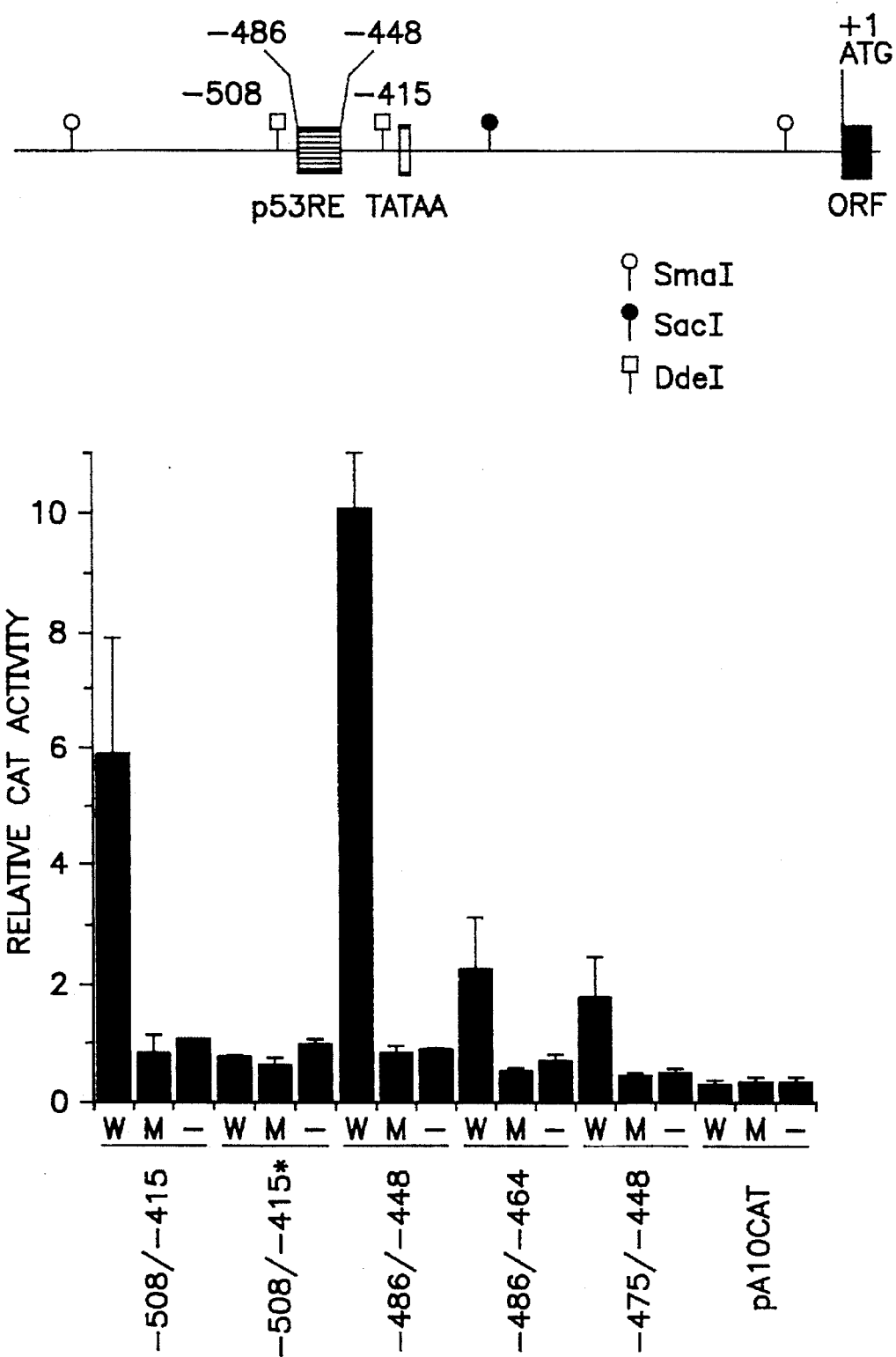
FIG. 10 shows the results of CAT assays, which demonstrate that the ⁻485 to ⁻449 bp region of the bax promotor (SEQ ID NO: 27) and fragments thereof confer p53-mediated regulation on a heterologous gene. Various fragments of the bax promotor were subcloned upstream of a minimal promotor in the plasmid pA10-CATBS and cotransfected into H358 cells with plasmids encoding a wild-type p53 protein (W), the mutant p53$^{179}$ protein (M) or no p53 protein (−) (see Example III). The region of the bax promotor that was analyzed is shown schematically at the top of the figure. CAT activity was measured 2 days after cotransfection and normalized relative to β-galactosidase (β-gal; mean ± SD; n=3).

The p53-RE$^U$ was further delineated by examining the expression of CAT from constructs containing various portions of the bax promotor as described in Example III.B., above. Expression of CAT constructs containing the 94 bp Dde I fragment (positions ⁻508 to ⁻415 of the bax promotor; SEQ ID NO: 26) was up-regulated approximately 6 to 8 fold when cotransfected with pCMV-p53$_{wt}$ as compared to cells that received plasmids encoding the mutant p53$^{179}$ or no p53 protein (FIG. 10). Expression of CAT constructs containing mutations in the potential p53-binding sites were unresponsive to p53 (FIG. 10). These results indicate that the ⁻508 to ⁻415 sequence of the bax promotor (SEQ ID NO: 26) confers p53-dependent up-regulation on a heterologous promotor.

The four potential p53 binding sites in the bax promotor are contained within a 37 bp region (positions ⁻485 to ⁻449; SEQ ID NO: 27). Cotransfection of a CAT construct containing the entire 37 bp sequence into H358 cells with a plasmid encoding wild-type p53 produced an approximately 10× to 15× increase in CAT activity. In contrast, H358 cells cotransfected with this CAT construct and a plasmid expressing the mutant p53$^{179}$ protein or no p53 protein showed minimal CAT activity (FIG. 10). These results establish that the 37 bp sequence at positions ⁻485 to ⁻449 of the bax promotor (SEQ ID NO: 27) confers p53-mediated regulation of a heterologous gene.

CAT constructs containing either the 5'- or 3'-half of the 37 bp p53-RE$^U$ also were cotransfected with the various p53 plasmids. The 5'-half CAT construct contains positions ⁻485 to ⁻465 bp (SEQ ID NO: 28), which includes the perfect 10 bp consensus p53 binding sequence flanked upstream by one imperfect sequence (7/10 matches) (FIG. 10). The 3'-half CAT construct contains positions ⁻474 to ⁻449 (SEQ ID NO: 29), which includes the perfect 10 bp consensus sequence and two downstream imperfect potential p53 binding sites.

In comparison to the results obtained using the entire 37 bp p53-RE$^U$, which conferred about a 10 to 15 fold increased level of CAT gene expression, wild-type p53 induced about a 2 to 5 fold up-regulation of CAT activity from constructs containing either the 5'-half or 3'-half of the p53-RE$^U$ (FIG. 10). These results demonstrate that a p53-RE$^U$ consisting of a perfect 10 bp consensus p53 binding sequence and at least one imperfect p53 binding site can confer p53-mediated up-regulation of a heterologous gene. Cotransfection experiments performed with the minimal promotor plasmid, pA10-CAT, lacking any elements from the bax gene confirmed the specificity of these results (see FIG. 10).

D. The p53 protein binds the p53-RE$^U$

This section describes a method for determining that wild-type p53 specifically binds to the p53-RE$^U$ present in the bax promotor.

In vitro-translated wild-type and mutant p53$^{179}$ proteins were prepared from RNA generated using the T7 RNA polymerase binding sites in the plasmids pCMV-p53$_{wt}$ and pCMV-p53$_{179}$. Coupled in vitro transcription/translation reactions were performed using T7 RNA polymerase and reticulocyte lysates (TNT-Lysate™; Promega, Inc.; Madison Wis.) as suggested by the manufacturer. Oligomers A and D were annealed and filled-in and radiolabelled using Klenow fragment in the presence of dATP, dGTP, TTP and $\alpha$-$^{32}$P-dCTP.

A mutant DNA probe also containing four nucleotide substitutions was prepared using 5'-GATCTCACAATTTAGAGATAATGCTG-3' (SEQ ID NO: 22) and 5'-TCGACAATATAGCCTACGCCCAGCATTATCTC-3' (SEQ ID NO: 23) oligomers. The mutant DNA probe contains nucleotide substitutions in three of the four p53 binding site motifs.

Approximately 5 µl of the p53 protein-containing translation product was preincubated with no further additions or with the following monoclonal antibodies: either a combination of 0.5 µg anti-p53 IgG2$_a$ clone DO-1 (Santa Cruz Biotechnology, Inc.) and 0.5 µg P421 (Oncogene Science, Inc.) or 1 µg anti-CD2 control IgG$_{2a}$ antibody Leu-5b (Becton-Dickinson, Inc.; San Jose Calif.). The reactions were incubated for 10 min at 25° C. with 0.5 µg sonicated salmon sperm DNA and 7 µl EMSA buffer (20 mM HEPES, pH 7.5, 0.1M NaCl, 1.5 mM MgCl$_2$, 10 mM dithiothreitol, 20% glycerol, 0.1% Triton X100, 1 mM PMSF, 10 ug/ml pepstatin, 10 ug/ml leupeptin). The $^{32}$P-labelled DNA probes (4×10$^5$ cpm) were added and incubation was continued for 20 min at 25° C. Following incubation, the samples were separated by electrophoresis in non-denaturing 4% polyacrylamide gels using 1× TBE, then the gels were dried and exposed to X-ray film (XAR; Kodak, Inc.) at −80° C. with intensifying screens.

Figure 11:
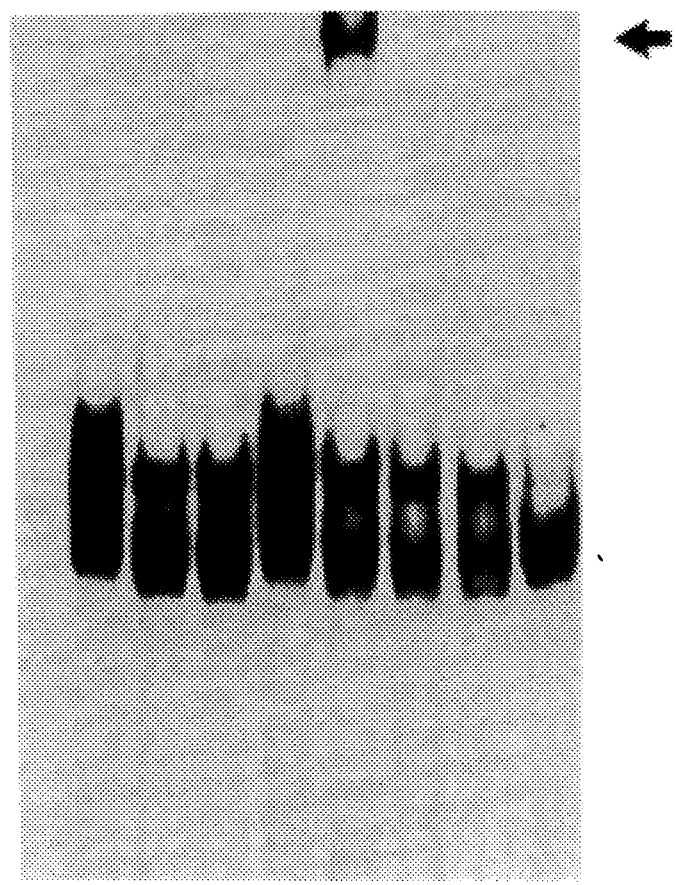
FIG. 11 demonstrates that p53 can bind in vitro to an oligonucleotide probe containing the ⁻485 to ⁻449 region of the bax promotor (SEQ ID NO: 27). Reticulocyte lysates containing wild-type p53 (wt), mutant p53$^{179}$ (mt) or no p53 protein (*) were incubated with $^{32}$P-labelled probes containing the ⁻485 to ⁻449 region of bax (wt) or a mutant sequence having four nucleotide substitutions (mt), with (+) or without (−) monoclonal antibodies against p53 or with the control antigen CD2, as indicated. DNA-protein complexes were fractionated in non-denaturing polyacrylamide gels and detected by autoradiography. The arrow indicates the presence of a super-shifted complex. In lane 1, the DNA probe, which was not incubated with reticulocyte lysate or antibodies, migrated off the gel.

FIG. 11 shows the results of the binding assays using the 37 bp p53-RE$^U$ or the mutant p53 binding element and wild-type or mutant p53$^{179}$ protein. Anti-p53 antibodies were included in some experiments to stabilize the in vitro interaction of p53 with the target DNA (Hupp et al., *Cell* 71:875–886 (1992), which is incorporated herein by reference). A moderate amount of non-specific binding of the in vitro-translated proteins occurred with both the wild-type and mutant DNA probes, regardless of whether p53 protein was present in the translation mixture (lanes 2–9).

When the binding reaction was performed using a combination of wild-type p53 protein, wild-type DNA probe and anti-p53 antibody was employed, a complex with shifted gel-mobility was detected (lane 6). No complex was observed when either the anti-p53 antibody or p53 protein was eliminated from the reaction (lanes 3 and 5). Furthermore, no complex formation was observed when substitution of either 1) mutant p53 for wild-type p53 protein, 2) mutant DNA probe for the wild-type sequence, or 3) an isotype- and subclass-matched monoclonal antibody to CD2 for the anti-p53 antibody was made in the reaction (lanes 7–9). These results demonstrate that p53 specifically interacts with the 37 bp p53-RE$^U$ and indicate that up-regulation from the p53-RE$^U$ as demonstrated using the CAT assays described above is due to p53 binding to this element.

EXAMPLE IV

Screening Assays for Identifying an Agent that Effectively Increases the Level of Cell Death This example describes screening assays that are useful for identifying an agent that can act as a p53 analog and, therefore, can induce apoptosis in a cell.

A. Cotransfection assay using a p53-null cell line

Cotransfection of a p53-null cell line such as H358 cells with a plasmid expressing a mutant p53 protein such as a temperature-sensitive p53 protein (Yonish-Rouach et al., 1991) and a plasmid containing a p53-RE linked to a reporter gene such as CAT is useful for obtaining a cell line that can be used to screen for an agent that effectively increases the level of cell death in a population of cells. The cell line obtained following transfection provides a well defined system having a known p53 protein and a known p53-RE.

A screening assay using cells such as those described above is particularly useful for identifying an effective agent that either 1) confers upon a mutant p53 protein the ability to act like a wild-type p53 tumor suppressor or 2) itself acts as a p53-analog in regulating expression of a gene that is involved in cell death and contains a p53-RE. These different mechanisms of action can be distinguished using the assay described in Example IV.C. An additional advantage of these cells is that a sample of the cells can be incubated at the permissive temperature, which allows for expression of the wild-type p53 tumor suppressor. Thus, the level of regulation achieved by the wild-type p53 and can be compared to the level of regulation obtained by various potentially effective agents.

Typically, the assay is performed in 96-well plates, which allows screening of a large number of agents in parallel. Various reporter genes can be used in the assay. However, a gene such as the luciferase gene provides the advantage that, following addition of the agent, the 96-well plates can be automatically scanned by a luminescence detector to identify those agents that desirably modulate the level of expression of the reporter gene. For example, if the p53-RE$^{TM}$ is linked to the reporter gene, an agent that decreased the luciferase activity would be considered an effective agent. Alternatively, if the p53-RE$^U$ is linked to the reporter gene, an effective agent would increase the level of expression of the reporter gene.

In some cases, an agent that is determined to be an effective agent in this assay can be further examined using the following assay, which provides the advantage that the effective agent can be examined in a cell obtained from a patient.

B. Transfection assay using a cell line that expresses a mutant p53 protein

This assay uses a cell such as a tumor cell that expresses a mutant p53 gene and is obtained from a cancer patient. In this case, the cell is transfected only with a plasmid containing p53-RE linked to a reporter gene and various agents are screened as described above. This assay is particularly advantageous in that an effective agent obtained using the assay of Example III.A. can be screened for its ability to induce apoptosis in a particular tumor cell obtained from a patient. Thus, the assay allows the selection of the most effective agent for a particular patient.

In addition, the assay can be used to select, from a pre-selected panel of effective agents, a effective agent that most effectively induces apoptosis in the particular patient's cancer cells. In this case, it is desirable to have previously screened agents using, for example, the cotransfection assay described above and to have preselected potentially effective agents.

C. Transfection assay using a p53-null cell line

Transfection of a p53-null cell line with a plasmid containing the p53-RE linked to a reporter gene provides a cell line that useful for screening to identify an agent that act as a p53 analog in a cell. The assay is performed as described in Example IV.A. and can be used to identify an effective agent that can independently provide the function of a wild-type p53 in regulating expression of a gene containing a p53-RE. This assay can be particularly useful when the p53-null cells are obtained from a cancer patient and the effective agent that is identified can be used to treat the patient.

EXAMPLE V

Screening Assays for Identifying an Agent that Effectively Inhibits p53-Mediated Regulation of the p53-RE This example describes screening assays that are useful for identifying an agent that can prevent the p53-mediated regulation of a gene containing the p53-RE and, therefore, can reduce or inhibit apoptosis in a cell.

A. Gel shift assay

The gel shift assay described above provides a simple and efficient method of screening various agents to identify an agent that effectively inhibits the ability of p53 to regulate expression of a gene containing the p53-RE. The method can be automated and, therefore, allows for the rapid screening of a large number of potentially effective agents.

This binding reactions are performed essentially as described in Example II.E. and Example III.D., except that the reactions are performed in 96-well plates and various agents are added to the well as appropriate. Following incubation of the samples can be transferred in parallel to precast gels for separation of the reaction products. Effective agents are selected by identifying those agents that inhibit the binding of p53 to a p53-RE. If desired, the selected effective agents can be further examined using the assays described below.

B. Cotransfection assay using a p53-null cell line

Cotransfection of a p53-null cell line such as H358 cells with a plasmid expressing a wild-type p53 tumor suppressor and a plasmid containing the p53-RE linked to a reporter gene such as CAT can provide cells that are useful for identifying agents that effectively inhibit the ability of p53 to regulate expression of a gene containing a p53-RE. These assays are performed as described in Example IV.A.

C. Transfection of a cell expressing a wild-type p53 tumor suppressor

Transfection of a cell that expresses wild-type p53 with a plasmid containing the p53-RE linked to a reporter gene can be used to identify an agent that inhibits apoptosis in a cell. This assay is particularly useful when the cell that is transfected is particularly susceptible to cell death. An example of such a cell is a neuronal cell obtained, for example, from a patient with amyotrophic lateral sclerosis patient. In this case, an effective agent that is selected based on the particular cell type to be treated.

Alternatively, the cell can be either 1) a cell that is obtained, for example, from the American Tissue Type Culture and is known to exhibit the characteristics of a cell obtained from a patient having a particular disease such as ataxia telangiectasia or 2) a neuronal cell line such as the cell lines described by Behl et al. (1993) that is exposed, for example, to amyloid beta protein (ABP) or to glutamate and, therefore, is a model for the type of cell death that occurs in Alzheimer's disease or in stroke, respectively. In this case, the assay provides the advantage that the cell lines that are used in the assay are adapted for tissue culture.

Although the invention has been described with reference to the disclosed examples, it should be understood that various modifications can be made without departing from the spirit of the invention. Accordingly, the invention is limited only by the following claims.

We claim:

1. An isolated nucleotide sequence, comprising the bax promotor as shown in FIG. 9 (SEQ ID NO: 24) or a fragment of SEQ ID NO: 24 which comprises a P53 binding site and confers regulatory activity upon a gene.

2. The nucleotide sequence of claim 1, wherein said fragment comprises positions $^-687$ to $^{-318}$ of said bax promotor (SEQ ID NO:25).

3. The nucleotide sequence of claim 1, wherein said fragment comprises positions $^-508$ to $^-415$ of said bax promotor (SEQ ID NO: 26).

4. The nucleotide sequence of claim 1, wherein said fragment comprises positions $^-485$ to $^-449$ of said bax promotor (SEQ ID NO: 27).

5. The nucleotide sequence of claim 1, wherein said fragment comprises positions $^-485$ to $^-465$ of said bax promotor (SEQ ID NO: 28).

6. The nucleotide sequence of claim 1, wherein said fragment comprises positions $^-474$ to $^-449$ of said bax promotor (SEQ ID NO: 29).

* * * * *

UNITED STATES PATENT AND TRADEMARK OFFICE
CERTIFICATE OF CORRECTION

PATENT NO. : 5,659,024
DATED : August 19, 1997
INVENTOR(S) : Reed et al.

It is certified that error appears in the above-identified patent and that said Letters Patent is hereby corrected as shown below:

Column 10,
Line 63, please delete "Effect" and replace therefor -- B. Effect --.

Column 11,
Line 50, please delete "γ- ☐P-ATP(3000" and replace therefor -- γ-$^{32}$P-ATP(3000 --.

Column 15,
Line 6, please delete "pS3-RE$^D$" and replace therefor -- p53-RE$^D$ --.
Line 17, please delete "B-gal" and replace therefor -- β-gal --.
Line 21, please delete "The" and replace therefor -- B. The --.

Column 17,
Line 35, please delete -- "32P-labelled" and replace therefor -- $^{32}$P-labelled --.

Column 18,
Line 32, please delete "Kind III" and replace therefor -- Hind III --.
Line 47, please delete "3'0" and replace therefor -- 3' --.

Column 19,
Line 47, please delete "10.25M" and replace therefor -- 0.25M --.

Column 22,
Line 30, please delete "p53-RE $^{TM}$" and replace therefor -- p53-RE$^D$ --.

Column 37, claim 2,
Line 7, please delete "$^{-318}$" and replace therefor -- -318 --.

Signed and Sealed this

Twenty-fifth Day of December, 2001

Attest:

Attesting Officer

JAMES E. ROGAN
Director of the United States Patent and Trademark Office

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
      ( A ) LENGTH: 190 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:1:

```
GTAGACTGAT  ATTAACAATA  CTTACTAATA  ATAACGTGCC  TCATGAAATA  AAGATCCGAA      60

AGGAATTGGA  ATAAAAATTT  CCTGCGTCTC  ATGCCAAGAG  GGAAACACCA  GAATCAAGTG     120

TTCCGCGTGA  TTGAAGACAC  CCCCTCGTCC  AAGAATGCAA  AGCACATCCA  ATAAAATAGC     180

TGGATTATAA                                                                190
```

( 2 ) INFORMATION FOR SEQ ID NO:2:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:2:

TGCACCTGAG CGCCTTCAC                                                                                   19

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TAGCTGATTC GACCATTTGC CTGA                                                                             24

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCAGGAGAAA TCAAACAAAG G                                                                                21

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

ATGGCTCGCT CGGTGACCCT AG                                                                               22

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TCATGATGCT TGATCACATG TCTCG                                                                            25

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GCTACGTAAC ACAGTTCCAC                                                                                  20

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGAATTCGCG GTGATGGACG GGTCCGG                       27

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GGAATTCTCA GCCCATCTTC TTCCAGA                       27

( 2 ) INFORMATION FOR SEQ ID NO:10:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Arg  Thr  Ser  Pro  Leu  Arg  Pro  Leu  Val  Ala  Thr  Ala  Gly  Pro  Ala  Leu
1                   5                        10                    15

Ser  Pro  Val  Cys
                    20

( 2 ) INFORMATION FOR SEQ ID NO:11:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Cys  Pro  Glu  Leu  Thr  Leu  Glu  Gln  Pro  Pro  Gln  Asp  Ala  Ser  Thr  Lys
1                   5                        10                    15

Lys  Leu  Ser  Glu
                    20

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GCGAAGCTTG TAGACTGATA TTAAC                         25

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
GCGAAGCTTA TAATCCAGCT ATTTT                                    25
```

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
GATCTCACAA GTTAGAGACA AGCCTG                                   26
```

( 2 ) INFORMATION FOR SEQ ID NO:15:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
TCGACAGGCT TGTCTCTAAC TTGTGA                                   26
```

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
GATCGAGACC AAGCCTGGGC GTGGGCTATA TTG                           33
```

( 2 ) INFORMATION FOR SEQ ID NO:17:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
TCGACAATAT AGCCCACGCC CAGGCTTGTC TC                            32
```

( 2 ) INFORMATION FOR SEQ ID NO:18:

( i ) SEQUENCE CHARACTERISTICS:

(A) LENGTH: 26 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:18:

GAAGATCTGA GACGGGGTTA TCTCTT                26

(2) INFORMATION FOR SEQ ID NO:19:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:19:

CGCGTCGACT GAGTGGTTTT GTTTTTT               27

(2) INFORMATION FOR SEQ ID NO:20:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:20:

AAGTTAGAGA TAATGCTGGG CGTAGG               26

(2) INFORMATION FOR SEQ ID NO:21:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:21:

CCTACGCCCA GCATTATCTC TAACTT               26

(2) INFORMATION FOR SEQ ID NO:22:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (i i) MOLECULE TYPE: DNA (genomic)

(x i) SEQUENCE DESCRIPTION: SEQ ID NO:22:

GATCTCACAA TTTAGAGATA ATGCTG               26

(2) INFORMATION FOR SEQ ID NO:23:

(i) SEQUENCE CHARACTERISTICS:
    (A) LENGTH: 32 base pairs
    (B) TYPE: nucleic acid
    (C) STRANDEDNESS: single
    (D) TOPOLOGY: linear ( i i ) MOLECULE TYPE: DNA (genomic)

( x i ) SEQUENCE DESCRIPTION: SEQ ID NO:23:

| TCGACAATAT | AGCCTACGCC | CAGCATTATC | TC | | | 3 2 |
|---|---|---|---|---|---|---|

( 2 ) INFORMATION FOR SEQ ID NO:24:

( i ) SEQUENCE CHARACTERISTICS:
        ( A ) LENGTH: 972 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:24:

| CCTGCTGATC | TATCAGCACA | GATTAGTTTC | TGCCACTTTT | TAAACTTCAT | ATTCCTTTTC | 60 |
|---|---|---|---|---|---|---|
| TTTTTACACA | AACACAAACA | TTCGAGTCAT | GACTGGGTGG | GGTGGCTCAA | GCCTGTAATC | 120 |
| TCAGCACTTT | GGGAGGCCAA | GGTGCGAGGA | TGCTTGAGTC | TGGGAGTTCA | GAGACCAGCC | 180 |
| TGGGCAACAT | AGAGAGACCT | CATCTCCACA | TAAAAGTTT | TAAAATTAA | CCAGGGGCGG | 240 |
| TGTAGTCCCA | GCTACTCAGG | AGGCTGAGGT | GGGAGGCTTC | AGCCCGGGAA | TTCCAGACTG | 300 |
| CAGTGAGCCA | TGATTGGGCC | ACTGCACTCC | AGCCTGGGCA | ACACAGTGAG | ACCCTGTCTC | 360 |
| AAAAAAAAA | AAAAAAAAA | AAAAAAAAC | AGGAAAAAAC | AAACAAACAG | AAAAGCAGGC | 420 |
| CTGGCGCGGT | AGCTCATGCC | TGTAATCCCA | GCGCTTTGGA | AGGCTGAGAC | GGGGTTATCT | 480 |
| CTTGGGCTCA | CAAGTTAGAG | ACAAGCCTGG | GCGTGGGCTA | TATTGCTAGA | TCCAGGTCTC | 540 |
| TGCAAAAAAC | AAACCACTC | AGTTTTTAGT | CATCTATAAC | GTCCTGCCTG | AAGCATGCT | 600 |
| ATTTGGGCC | TCTGAGCTTT | TGCACTTGCT | AATTCCTTCT | GCGCTGGGGA | GAGCTCAAAC | 660 |
| CCTGCCCGAA | ACTTCTAAAA | ATGGTGCCTG | GATAAATGAA | GGCATTAGAG | CTGCGATTGG | 720 |
| ACGGGCGGCT | GTTGGACGGC | GCCACTGCTG | GNACTTATCG | GAGATGCTC | ATTGGACAGT | 780 |
| CACGTGACGG | GACCAAACCT | CCCGAGGGAG | CGAGGCAGGT | GCGGTCACGT | GACCCGGCGG | 840 |
| CGCTGCGGGG | CAGCGGCCAT | TTTGCGGGGC | GGCCACGTGA | AGGACGCACG | TTCAGCGGGG | 900 |
| CTCTCACGTG | ACCCGGGCGC | GCTGCGGCCG | CCCGCGCGGA | CCCGGCGAGA | GGCGGCGGCG | 960 |
| GGAGCGGCGG | TG | | | | | 972 |

( 2 ) INFORMATION FOR SEQ ID NO:25:

( i ) SEQUENCE CHARACTERISTICS:
        ( A ) LENGTH: 370 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:25:

| GGGAATTCCA | GACTGCAGTG | AGCCATGATT | GGGCCACTGC | ACTCCAGCCT | GGGCAACACA | 60 |
|---|---|---|---|---|---|---|
| GTGAGACCCT | GTCTCAAAAA | AAAAAAAAA | AAAAAAAAA | AAAACAGGAA | AAACAAACA | 120 |
| AACAGAAAAG | CAGGCCTGGC | GCGGTAGCTC | ATGCCTGTAA | TCCCAGCGCT | TTGGAAGGCT | 180 |
| GAGACGGGGT | TATCTCTTGG | GCTCACAAGT | TAGAGACAAG | CCTGGGCGTG | GGCTATATTG | 240 |
| CTAGATCCAG | GTCTCTGCAA | AAAACAAAAC | CACTCAGTTT | TTAGTCATCT | ATAACGTCCT | 300 |
| GCCTGGAAGC | ATGCTATTTT | GGGCCTCTGA | GCTTTGCAC | TTGCTAATTC | CTTCTGCGCT | 360 |
| GGGGAGAGCT | | | | | | 370 |

( 2 ) INFORMATION FOR SEQ ID NO:26:

( i ) SEQUENCE CHARACTERISTICS:
        ( A ) LENGTH: 94 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:26:

```
TGAGACGGGG  TTATCTCTTG  GGCTCACAAG  TTAGAGACAA  GCCTGGGCGT  GGGCTATATT        60

GCTAGATCCA  GGTCTCTGCA  AAAACAAAA  CCAC                                      94
```

( 2 ) INFORMATION FOR SEQ ID NO:27:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:27:

```
TCACAAGTTA  GAGACAAGCC  TGGGCGTGGG  CTATATT                                   37
```

( 2 ) INFORMATION FOR SEQ ID NO:28:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:28:

```
TCACAAGTTA  GAGACAAGCC  T                                                     21
```

( 2 ) INFORMATION FOR SEQ ID NO:29:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:29:

```
AGACAAGCCT  GGGCGTGGGC  TATATT                                                26
```

( 2 ) INFORMATION FOR SEQ ID NO:30:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:30:

```
RRRCWWGYYY                                                                    10
```